US012793808B2

(12) United States Patent
Nance et al.

(10) Patent No.: US 12,793,808 B2
(45) Date of Patent: Nov. 10, 2026

(54) METHODS AND SYSTEMS FOR DIFFERENTIATING SOMATIC AND GERMLINE VARIANTS

(71) Applicant: GUARDANT HEALTH, INC., Redwood City, CA (US)

(72) Inventors: Tracy Nance, Redwood City, CA (US); Elena Helman, Redwood City, CA (US); Darya Chudova, San Jose, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 174 days.

(21) Appl. No.: 16/823,937

(22) Filed: Mar. 19, 2020

(65) Prior Publication Data

US 2020/0327954 A1 Oct. 15, 2020

Related U.S. Application Data

(63) Continuation of application No. PCT/US2018/052087, filed on Sep. 20, 2018.

(60) Provisional application No. 62/561,048, filed on Sep. 20, 2017.

(51) Int. Cl.

| | |
|---|---|
| ***G16B 5/00*** | (2019.01) |
| ***C12P 19/34*** | (2006.01) |
| ***C12Q 1/6869*** | (2018.01) |
| ***G06F 17/18*** | (2006.01) |

(52) U.S. Cl.
CPC ................ *G16B 5/00* (2019.02); *C12P 19/34* (2013.01); *C12Q 1/6869* (2013.01); *G06F 17/18* (2013.01)

(58) Field of Classification Search
CPC ........... G16B 5/00; G16B 30/00; C12P 19/34; C12Q 1/6869; G06F 17/18
See application file for complete search history.

(56) References Cited

U.S. PATENT DOCUMENTS

| | | | |
|---|---|---|---|
| 5,912,148 | A | 6/1999 | Eggerding |
| 6,130,073 | A | 10/2000 | Eggerding |
| 6,210,891 | B1 | 4/2001 | Nyren et al. |
| 6,258,568 | B1 | 7/2001 | Nyren |
| 6,582,908 | B2 | 6/2003 | Fodor et al. |
| 6,818,395 | B1 | 11/2004 | Quake et al. |
| 6,833,246 | B2 | 12/2004 | Balasubramanian |
| 6,858,412 | B2 | 2/2005 | Willis et al. |
| 6,964,846 | B1 | 11/2005 | Shuber |
| 7,035,943 | B2 | 4/2006 | Yamane et al. |
| 7,163,789 | B2 | 1/2007 | Chen et al. |
| 7,169,560 | B2 | 1/2007 | Lapidus et al. |
| 7,282,335 | B2 | 10/2007 | Gocke et al. |
| 7,282,337 | B1 | 10/2007 | Harris |
| 7,302,146 | B2 | 11/2007 | Turner et al. |
| 7,313,308 | B2 | 12/2007 | Turner et al. |
| 7,449,184 | B2 | 11/2008 | Allison et al. |
| 7,476,503 | B2 | 1/2009 | Turner et al. |
| 7,482,120 | B2 | 1/2009 | Buzby |
| 9,834,822 | B2 | 12/2017 | Talasaz |
| 9,840,743 | B2 | 12/2017 | Talasaz |
| 2001/0053519 | A1 | 12/2001 | Fodor et al. |
| 2003/0152490 | A1 | 8/2003 | Trulson et al. |
| 2011/0160078 | A1 | 6/2011 | Fodor et al. |
| 2013/0288244 | A1 | 10/2013 | Deciu et al. |
| 2014/0100121 | A1 | 4/2014 | Lo et al. |
| 2014/0296081 | A1 | 10/2014 | Diehn et al. |
| 2015/0368708 | A1 | 12/2015 | Talasaz |
| 2016/0046986 | A1 | 2/2016 | Eltoukhy et al. |
| 2016/0201131 | A1 | 7/2016 | Wang et al. |
| 2016/0232290 | A1 | 8/2016 | Rava et al. |
| 2017/0058332 | A1 | 3/2017 | Kermani et al. |
| 2017/0073774 | A1 | 3/2017 | Lo et al. |
| 2018/0080068 | A1 * | 3/2018 | Kamps-Hughes ..... G16B 30/00 |
| 2018/0251848 | A1 | 9/2018 | Diehn et al. |
| 2019/0362808 | A1 * | 11/2019 | Halperin .............. G01N 33/574 |
| 2020/0075124 | A1 * | 3/2020 | Zhao .................... C12Q 1/6827 |
| 2020/0202224 | A1 | 6/2020 | Lanman et al. |
| 2020/0370129 | A1 * | 11/2020 | Quinn .................... G16B 20/40 |
| 2021/0343372 | A1 * | 11/2021 | Tell ........................ G16B 30/10 |
| 2023/0245788 | A1 | 8/2023 | Colley et al. |

FOREIGN PATENT DOCUMENTS

| | | | |
|---|---|---|---|
| JP | 2015535681 | A | 12/2015 |
| WO | 2013142389 | A1 | 9/2013 |
| WO | 2014151117 | A1 | 9/2014 |
| WO | 2015164432 | A1 | 10/2015 |
| WO | 2016109452 | A1 | 7/2016 |
| WO | 2016127944 | A1 | 8/2016 |
| WO | 2016149261 | A1 | 9/2016 |
| WO | 2021076775 | A1 | 4/2021 |

OTHER PUBLICATIONS

Zhang, H. Osimertinib making a breakthrough in lung cancer targeted therapy. OncoTargets and Therapy, 9:5489-5493. (Year: 2016).*

(Continued)

*Primary Examiner* — Janna Nicole Schultzhaus
(74) *Attorney, Agent, or Firm* — Stephen W. Chen

(57) ABSTRACT

In an aspect, a method of identifying a somatic or germline origin of a nucleic acid variant from a sample of nucleic acid molecules comprises: determining quantitative measures for the nucleic acid variant comprising total allele count and minor allele count for the nucleic acid variant; identifying an associated variable of the nucleic acid variant; determining quantitative value for the associated variable; generating a statistical model for expected germline mutant allele counts at a genomic locus of the nucleic acid variant; generating a probability value (p-value) for the nucleic acid variant based at least in part on the statistical model, the quantitative value, and at least one of the quantitative measures; and classifying the nucleic acid variant as (i) being of somatic origin when the p-value is below a predetermined threshold value, or as (ii) being of germline origin when the p-value is at or above the predetermined threshold value.

18 Claims, 6 Drawing Sheets

(56) References Cited

OTHER PUBLICATIONS

Office Action in Japanese Patent Application No. 2019-563118, dated Feb. 7, 2022.
Sun, J.X. et al. "A computational approach to distinguish somatic vs. germline origin of genomic alterations from deep sequencing of cancer specimens without a matched normal" PLoS Comp Bio (2018) 14(2):e1005965.
Plagnol, V. et al. "A robust model for read count data in exome sequencing experiments and implications for copy number variant calling" Bioinformatics (2012) 28(21):2747-2754.
Singapore Written Opinion for Application No. 11202002381T dated Oct. 28, 2021.
Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.
Extended European search report and opinion dated Apr. 19, 2021 for EP Application No. 18802961.5.
Goode, D.L. et al. "A simple consensus approach improves somatic mutation prediction accuracy" Genome Med j (2013) 5(9):90.
Henaff, E. et al. "Jitterbug: Somatic and Germline Transposon Insertion Detection at Single-Nucleotide Resolution" BMC Genomics Oct. 12, 2015 16(768):1-16; p. 3, col. 2, paragraph 1; DOI:1186/s12864-015-1975-5.
Hu, Y. et al. "Discrimination of Germline EGFR T790M Mutations in Plasma Cell-Free DNA Allows Study of Prevalence Across 31,414 Cancer Patients" Clin Cancer Res. Dec. 2017; 23(23): 7351-7359.
International search report and written opinion dated Feb. 5, 2019 for PCT/US2019/052087.
International search report and written opinion dated Aug. 31, 2018 for PCT/US2018/033038.
Kockan, C. et al. "SiNVICT: ultra-sensitive detection of single nucleotide variants and indels in circulating tumour DNA" Bioinformatics (2017) 33(1):26-34.
Lek, M et al. "Analysis of protein-coding genetic variation in 60,706 humans" Nature. Aug. 2016; 536(7616): 285-291.
Murtaza, M. et al. "Non-invasive analysis of acquired resistance to cancer therapy by sequencing of plasma DNA" Nauter (May 2013) 497(7447):108-112.
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.
Phallen, J. et al. "Direct detection of early-stage cancers using circulating tumor DNA" Sci Trans Med (2017) vol. 9, Issue 403, eaan2415DOI: 10.1126/scitranslmed.aan2415.
Schrader, K.A. et al. "Germline Variants in Targeted Tumor Sequencing Using Matched Normal DNA" JAMA Oncol (2016) 2(1):104-111.
Shiraishi, Y. et al. "An empirical Bayesian framework for somatic mutation detection from cancer genome sequencing data" Nucl Acids Res (2013) 41(7):e89.
Skelly, D.A. et al. "A powerful and flxible statistical framework for testing hypotheses of allele-specific gene expression from RNA-seq data" Gen Res (2011) 1728-1737.
Smith, K.S. et al. "SomVarIUS: somatic variant identification from unpaired tissue samples" Bioinformatics (2016) 32(6):808-813.
Xu, H. et al. "Comparison of Somatic Mutation Calling Methods in Amplicon and Whole Exome Sequence Data" BMC Genomics Mar. 28, 2014; 15(244):1-10; p. 4, col. 2, paragraph 1; figures 2-3; DOI:10.1186/1471-2164-15-244.
Bennett et al., "Cell-free DNA and next-generation sequencing in the service of personalized medicine for lung cancer" Oncotarget (2016) 7(43):71013-71035.
Exam Report for European Patent Application No. 18786494.7 dated Sep. 18, 2023.
Kamps, R. et al. "Next-generation sequencing in oncology: genetic diagnosis, risk prediction and cancer classification" International J Mol Sci (2017) 18(2) 308:1-54.
Lanman, et al., Analytical and Clinical Validation of a Digital Sequencing Panel for Quantitative, Highly Accurate Evaluation of Cell-Free Circulating Tumor DNA PLoS One, Oct. 2015, 10(10), e0140712. doi:10.1371/journal.pone.0140712.
Final Office Action for U.S. Appl. No. 16/678,060, dated Jul. 15, 2024.
Frenel, J.S. et al. "Serial Next-Generation Sequencing of Circulating Cell-Free DNA Evaluating Tumor Clone Response to Molecularly Targeted Drug Administration" Clin Canc Res (2015) 21(20):4586-4596.
Garcia-Murillas, I. et al. "Mutation tracking in circulating tumor DNA predicts relapse in early breast cancer" Science (2015) 7(302):pp. 302ra133.
Siravegna, G. et al. "Clonal evolution and resistance to EGFR blockade in the blood of colorectal cancer patients" Nature Medicine (2015) 21(7):795-801.
Hassan, M. et al. "Innovations in Genomics and Big Data Analytics for Personalized Medicine and Health Care: A Review" J Mol. Sci (2022) 23(4645):1-17.
Morozova, O. et al. "Applications of next-generation sequencing technologies in functional genomics" Genomics (2008) 92(5):255-264.
Office Action for U.S. Appl. No. 16/678,060, Jun. 17, 2025.
Office Action for U.S. Appl. No. 19/098,448, dated Jul. 1, 2025.
Office Action for U.S. Appl. No. 19/170,971, dated Aug. 19, 2025.
Office Action for U.S. Appl. No. 19/170,982 dated Aug. 12, 2025.
Office Action for U.S. Appl. No. 19/170,988 dated Jun. 24, 2025.
Astier, Y. et al. "Toward Single Molecule DNA Sequencing: Direct Identification of Ribonucleoside and Deoxyribonucleoside 5'-Monophosphates by Using an Engineered Protein Nanopore Equipped with a Molecular Adapter" J Am Chem Soc (2006) 128(5):1705-1710.
Cock, PJA, et al. "The Sanger FASTQ file format for sequences with quality scores, and the Solexa/Illumina FASTQ variants" NAR (2009) 38(6):1767-1771.
Danecek, P. et al. "The variant call format and VCFtools" Bioinformatics (2011) 27(15):2156-2158.
Levy, S.E. et al. "Advancements in Next-Generation Sequencing" Ann Rev Genomics & Hum Genetics (2016) 17:95-115.
Li, et al., The Sequence Alignment/Map format and SAMtools, Bioinformatics, 2009, 25(16):2078-9.
Liu, L. et al. "Comparison of Next-Generation Sequencing Systems" J Biomed & Biotech (2012) Article ID251364:1-11.
MacLean, D. et al. "Application of 'next-generation' sequencing technologies to microbial genetics" Nature Rev Microbiol (2009) 7:287-296.
Ning, Z. et al. "SSAHA: A Fast Search Method for Large DNA Databases" Genome Res (2001) 11:1725-1729.
Office Action for U.S. Appl. No. 19/098,448, dated Mar. 13, 2026.
Voelkerding, K.V. et al. "Next-generation sequencing: from basic research to diagnostics" Clin Chem (2009) 55:641-658.
Final Office Action for U.S. Appl. No. 16/678,060 dated Nov. 3, 2025.
Final Office Action for U.S. Appl. No. 19/098,448, dated Oct. 22, 2025.
Final Office Action for U.S. Appl. No. 19/170,982 dated Dec. 15, 2025.
Final Office Action for U.S. Appl. No. 19/170,988 dated Oct. 8, 2025.
Krampis, et al., "A review of Cloud Computing Bioinformatics Solutions for Next-Gen Sequencing Data Analysis and Research", Methods Next-Generation Seq. (2015) 2:23-34.
Ocana, et al., "Parallel computing in genomic research: advances and applications" Advances and Applications in Bioinformatics and Chemistry (2015) , 8:23-35.

* cited by examiner

METHODS AND SYSTEMS FOR DIFFERENTIATING SOMATIC AND GERMLINE VARIANTS

CROSS-REFERENCE

This application is a continuation of International Patent Application No. PCT/US2018/052087, filed Sep. 20, 2018, which claims the benefit of U.S. Provisional Application No. 62/561,048, filed on Sep. 20, 2017, which application is incorporated herein by reference in its entirety.

BACKGROUND

An important aspect of cancer genomics is to precisely identify the origin of genetic alterations for appropriate treatment of patients. A recent study found that over 2% of advanced cancer patients may have unidentified germline alterations found incidentally during next-generation sequencing (NGS) for targetable somatic alterations. However, tissue-based NGS may not be able to accurately distinguish germline mutations from somatic mutations without comparison to normal tissue. In plasma, somatic variants typically occur at mutant allele fractions (MAFs) which may be 1-2 orders of magnitude lower than those of germline variants and hence liquid biopsy can accurately assign germline/somatic origin. However, certain factors such as allelic imbalance from copy number variation (CNV) or loss of heterozygosity (LOH) can skew germline MAFs away from the expected range for germline MAFs. Therefore, there is a need for methods that can take into account these factors in determining the origin of a variant.

SUMMARY

The present disclosure provides methods and systems for differentiating somatic and germline variants in a sample of nucleic acid molecules, such as cell-free deoxyribonucleic acid (cfDNA). Such methods may use common single nucleotide polymorphisms (SNPs) to model local germline allele count behavior and may distinguish somatic variants based on MAF deviation from the observed germline MAF.

In one aspect, the present disclosure provides a method of identifying a somatic or germline origin of a nucleic acid variant from a sample of nucleic acid molecules (e.g., a tissue sample, a sample of cell-free DNA, and/or the like). The method includes (a) determining one or more quantitative measures for the nucleic acid variant from the nucleic acid sample. The quantitative measures comprise a total allele count and minor allele count for the nucleic acid variant. The method also includes (b) identifying at least one associated variable of the nucleic acid variant from the nucleic acid sample and (c) determining a quantitative value for the associated variable of the nucleic acid variant. The method further includes (d) generating a statistical model for expected germline mutant allele counts at the genomic locus of the nucleic acid variant and (e) generating a probability value (p-value) for the nucleic acid variant based on the statistical model for expected germline allele counts and the quantitative value for the associated variable of the nucleic acid variant and at least one of the quantitative measures for the nucleic acid variant. In addition, the method also includes (f) classifying the nucleic acid variant (i) as being of somatic origin when the p-value of the nucleic acid variant is below a threshold value, or (ii) as being of germline origin when the p-value of the nucleic acid variant is at or above the threshold value.

In an aspect, the present disclosure provides a method of identifying a somatic or germline origin of a nucleic acid variant from a sample of cell-free nucleic acid molecules (e.g., cell-free deoxyribonucleic acid (cfDNA) molecules), the method comprising: (a) determining a plurality of quantitative measures for the nucleic acid variant from the sample of cell-free nucleic acid molecules, wherein the plurality of quantitative measures comprises a total allele count and a minor allele count for the nucleic acid variant; (b) identifying an associated variable of the nucleic acid variant from the sample of cell-free nucleic acid molecules; (c) determining a quantitative value for the associated variable of the nucleic acid variant; (d) generating a statistical model for expected germline mutant allele counts at a genomic locus of the nucleic acid variant; (e) generating a probability value (p-value) for the nucleic acid variant based at least in part on the statistical model for expected germline mutant allele counts, the quantitative value for the associated variable of the nucleic acid variant, and at least one of the plurality of quantitative measures for the nucleic acid variant; and (f) classifying the nucleic acid variant as (i) being of somatic origin when the p-value for the nucleic acid variant is below a predetermined threshold value, or as (ii) being of germline origin when the p-value for the nucleic acid variant is at or above the predetermined threshold value.

In some embodiments, the method further comprises obtaining the sample of cell-free nucleic acid molecules from a subject. In some embodiments, the method further comprises receiving sequencing information generated from the sample of cell-free nucleic acid molecules, wherein the sequencing information comprises cell-free nucleic acid sequencing reads comprising the nucleic acid variant and the associated variable of the nucleic acid variant, which associated variable comprises at least one heterozygous single nucleotide polymorphism (het SNP) within a specified genomic region relative to the nucleic acid variant. In some embodiments, the method further comprises sequencing nucleic acids from the sample of cell-free nucleic acid molecules to generate sequencing information, wherein the plurality of quantitative measures for the nucleic acid variant and the quantitative value for the associated variable are determined from the sequencing information.

In some embodiments, the method further comprises determining the plurality of quantitative measures for the nucleic acid variant, identifying the associated variable of the nucleic acid variant, and determining the quantitative value for the associated variable from sequencing information generated from the sample of cell-free nucleic acid molecules. In some embodiments, the method further comprises generating the predetermined threshold value using a beta-binomial model of expected germline mutant allele counts for nucleic acids of the sample of cell-free nucleic acid molecules. In some embodiments, the method further comprises classifying the somatic or germline origin of a plurality of nucleic acid variants from a plurality of genomic loci in the sample of cell-free nucleic acid molecules.

In some embodiments, the associated variable of the nucleic acid variant comprises at least one heterozygous single nucleotide polymorphism (het SNP). In some embodiments, the associated variable of the nucleic acid variant comprises at least two het SNPs. In some embodiments, the associated variable of the nucleic acid variant comprises a genomic locus that is linked to a genomic locus that comprises the nucleic acid variant.

In some embodiments, the method further comprises determining a mean and/or a variance value of one or more mutant allele counts for the associated variable of the nucleic acid variant. In some embodiments, the method further comprises determining an average quantitative value for the associated variable of the nucleic acid variant. In some embodiments, the associated variable of the nucleic acid variant comprises one or more of: a heterozygous single nucleotide polymorphism (het SNP), a GC content measure, a probe-specific bias measure, a fragment length value, a sequencing statistics measure, a copy number breakpoint, and clinical data for a subject. In some embodiments, the method further comprises determining a mean and/or a variance value of the associated variable of the nucleic acid variant.

In some embodiments, the method further comprises determining a local germline folded mutant allele fraction (MAF), $\mu_{bin}$, for the nucleic acid variant, where bin is a gene or another specified genomic region comprising the nucleic acid variant and folded MAF is min(MAF, 1−MAF). In some embodiments, the specified genomic region is a region within about $10^1$, $10^2$, $10^3$, $10^4$, $10^5$, $10^6$, $10^7$, $10^8$, $10^9$, or $10^{10}$ base pairs of the nucleic acid variant. In some embodiments, the associated variable of the nucleic acid variant comprises at least one single nucleotide polymorphism (SNP) comprising a population allele frequency (AF) greater than about 0.001. In some embodiments, the associated variable of the nucleic acid variant comprises at least one non-oncogenic single nucleotide polymorphism (SNP). In some embodiments, the associated variable of the nucleic acid variant comprises at least one single nucleotide polymorphism (SNP) comprising a mutant allele fraction (MAF) less than about 0.9.

In some embodiments, the associated variable comprises at least one heterozygous single nucleotide polymorphism (SNP) within a specified genomic region relative to the nucleic acid variant, and wherein the method comprises estimating beta binomial distribution parameters using: (x, y)~Beta binomial($\mu_{bin}$, ρ), wherein y=a vector of total molecule count of the at least one germline heterozygous SNP, with one entry for each germline heterozygous SNP; x=a vector of min(mutant allele count of the at least one germline heterozygous SNP, y—mutant allele count of the at least one germline heterozygous SNP), with one entry for each germline heterozygous SNP; $\mu_{bin}$=an estimate of the mean mutant allele count of heterozygous SNPs in a bin, wherein the bin is the specified genomic region relative to the nucleic acid variant; and ρ=an estimate of a dispersion parameter. In some embodiments, the method further comprises calculating an upper bound and a lower bound for the p-value. In some embodiments, the method further comprises calculating a two-tailed p-value for the nucleic acid variant using: p-value=2*min($Pr_{bb}(x'>A|\mu_{bin}, \rho, B)$, $Pr_{bb}(x'<A|\mu_{bin}, \beta, B)$), wherein $Pr_{bb}$=a probability of beta binomial; x'=a random variable distributed with the beta binomial; A=a mutant allele count of the nucleic acid variant; and B=a total molecule count of the nucleic acid variant. In some embodiments, ρ comprises a median value of at least one set of ρ values from a historic sample set. In some embodiments, the method further comprises replacing the median ρ parameter with a function of GC content of nucleic acid variant. In some embodiments, the method further comprises determining a maximum likelihood estimate of $\mu_{bin}$. In some embodiments, the method further comprises determining a mean estimate of $\mu_{bin}$. In some embodiments, the method further comprises determining a maximum likelihood estimate of ρ. In some embodiments, the method further comprises determining a variance estimate of ρ. In some embodiments, the method further comprises generating a report in electronic and/or paper format with provides an indication of the classification of the nucleic acid variants as being of either somatic or germline origin.

In another aspect, the present disclosure provides a non-transitory computer-readable medium comprising computer-executable instructions which, when executed by at least one electronic processor, perform a method comprising: (a) determining a plurality of quantitative measures for a nucleic acid variant from sequencing information generated from a sample of cell-free nucleic acid molecules (e.g., cell-free deoxyribonucleic acid (cfDNA) molecules), wherein the plurality of quantitative measures comprises a total allele count and a minor allele count for the nucleic acid variant; (b) identifying an associated variable of the nucleic acid variant from the sequencing information; (c) determining a quantitative value for the associated variable of the nucleic acid variant; (d) generating a statistical model for expected germline mutant allele counts at a genomic locus of the nucleic acid variant; (e) generating a probability value (p-value) for the nucleic acid variant based at least in part on the statistical model for expected germline mutant allele counts, the quantitative value for the associated variable of the nucleic acid variant, and at least one of the plurality of quantitative measures for the nucleic acid variant; and (f) classifying the nucleic acid variant as (i) being of somatic origin when the p-value of the nucleic acid variant is below a predetermined threshold value, or as (ii) being of germline origin when the p-value for the nucleic acid variant is at or above the predetermined threshold value.

In some embodiments, the predetermined threshold value is generated using a beta-binomial model of expected germline mutant allele counts for the sample of cell-free nucleic acid molecules (e.g., cfDNA molecules). In some embodiments, the associated variable of the nucleic acid variant comprises at least one heterozygous single nucleotide polymorphism (het SNP). In some embodiments, the associated variable of the nucleic acid variant comprises at least two het SNPs. In some embodiments, the associated variable of the nucleic acid variant comprises a genomic locus that is linked to a genomic locus that comprises the nucleic acid variant. In some embodiments, a mean and/or a variance value of one or more mutant allele counts is determined for the associated variable of the nucleic acid variant. In some embodiments, at least one of the plurality of quantitative measures comprises a number of nucleic acid molecules of the sample of cell-free nucleic acid molecules that comprise the nucleic acid variant. In some embodiments, the associated variable of the nucleic acid variant comprises one or more of: a heterozygous single nucleotide polymorphism (het SNP), a GC content measure, a probe-specific bias measure, a fragment length value, a sequencing statistics measure, a copy number breakpoint, and clinical data for a subject.

In some embodiments, a local germline folded mutant allele fraction (MAF), $\mu_{bin}$, is determined for the nucleic acid variant, where bin is a gene or another specified genomic region comprising the nucleic acid variant and folded MAF is min(MAF, 1−MAF). In some embodiments, the specified genomic region is a region within about $10^1$, $10^2$, $10^3$, $10^4$, $10^5$, $10^6$, $10^7$, $10^8$, $10^9$, or $10^{10}$ base pairs of the nucleic acid variant. In some embodiments, the associated variable of the nucleic acid variant comprises at least one single nucleotide polymorphism (SNP) comprising a population allele frequency (AF) greater than about 0.001. In some embodiments, the associated variable comprises at least one non-oncogenic single nucleotide polymorphism (SNP). In some embodiments, the associated variable of the nucleic acid variant comprises at least one single nucleotide polymorphism (SNP) comprising a mutant allele fraction (MAF) less than about 0.9.

In some embodiments, the associated variable comprises at least one heterozygous single nucleotide polymorphism (SNP) within a specified genomic region relative to the nucleic acid variant, and wherein beta binomial distribution parameters are estimated using: (x, y)~Beta binomial($\mu_{bin}$, ρ), wherein y=a vector of total molecule count of the at least one germline heterozygous SNP, with one entry for each of the at least one germline heterozygous SNP; x=a vector of min (mutant allele count of the at least one germline heterozygous SNP, y—mutant allele count of the at least one germline heterozygous SNP), with one entry for each of the at least one germline heterozygous SNP; $\mu_{bin}$=an estimate of the mutant allele count of heterozygous SNPs in a bin, wherein the bin is the specified genomic region relative to the nucleic acid variant; and ρ=an estimate of a dispersion parameter. In some embodiments, an upper bound and a lower bound for the p-value are calculated. In some embodiments, a two-tailed p-value for the nucleic acid variant is calculated using:

$$p\text{-value}=2*\min(Pr_{bb}(x'>x|\mu_{bin},\rho,B),Pr_{bb}(x'<x|\mu_{bin},\rho,B)),$$

wherein $Pr_{bb}$=a probability of beta binomial; x'=a random variable distributed with the beta binomial; A=a mutant allele count of the nucleic acid variant; and B=a total molecule count of the nucleic acid variant.

In another aspect, the present disclosure provides a system, comprising a controller comprising, or capable of accessing, a non-transitory computer-readable medium comprising computer-executable instructions which, when executed by at least one electronic processor, perform a method comprising: (a) determining a plurality of quantitative measures for a nucleic acid variant from sequencing information generated from a sample of nucleic acid molecules (e.g., a sample of cell-free deoxyribonucleic acid (cfDNA) molecules), wherein the plurality of quantitative measures comprises a total allele count and a minor allele count for the nucleic acid variant; (b) identifying an associated variable of the nucleic acid variant from the sequencing information; (c) determining a quantitative value for the associated variable of the nucleic acid variant; (d) generating a statistical model for expected germline mutant allele counts at a genomic locus of the nucleic acid variant; (e) generating a probability value (p-value) for the nucleic acid variant based at least in part on the statistical model for expected germline mutant allele counts, the quantitative value for the associated variable of the nucleic acid variant, and at least one of the plurality of quantitative measures for the nucleic acid variant; and (f) classifying the nucleic acid variant as (i) being of somatic origin when the p-value of the nucleic acid variant is below a predetermined threshold value, or as (ii) being of germline origin when the p-value for the nucleic acid variant is at or above the predetermined threshold value.

In some embodiments, the system comprises a nucleic acid sequencer operably connected to the controller, which nucleic acid sequencer is configured to provide the sequencing information from nucleic acids of the sample of nucleic acid molecules (e.g., cell-free nucleic acid molecules). In some embodiments, the system comprises a sample preparation component operably connected to the controller, which sample preparation component is configured to prepare nucleic acids of the sample to be sequenced by a nucleic acid sequencer. In some embodiments, the system comprises a nucleic acid amplification component operably connected to the controller, which nucleic acid amplification component is configured to amplify nucleic acids of the sample. In some embodiments, the system comprises a material transfer component operably connected to the controller, which material transfer component is configured to transfer one or more materials between a nucleic acid sequencer and a sample preparation component.

In some embodiments, the predetermined threshold value is generated using a beta-binomial model of expected germline mutant allele counts for nucleic acids of the sample (e.g., cfDNA molecules). In some embodiments, the associated variable of the nucleic acid variant comprises at least one heterozygous single nucleotide polymorphism (het SNP). In some embodiments, the associated variable of the nucleic acid variant comprises at least two het SNPs. In some embodiments, the associated variable of the nucleic acid variant comprises a genomic locus that is linked to a genomic locus that comprises the nucleic acid variant.

In some embodiments, a mean and/or a variance value of one or more mutant allele counts is determined for the associated variable of the nucleic acid variant. In some embodiments, the p-value is used to classify the nucleic acid variant. In some embodiments, at least one of the plurality of quantitative measures comprises a number of nucleic acid molecules of the sample of cell-free nucleic acid molecules that comprise the nucleic acid variant. In some embodiments, the associated variable comprises one or more of: a heterozygous single nucleotide polymorphism (het SNP), a GC content measure, a probe-specific bias measure, a fragment length value, a sequencing statistics measure, a copy number breakpoint, and clinical data for a subject.

In some embodiments, a local germline folded mutant allele fraction (MAF), $\mu_{bin}$, is determined for the nucleic acid variant, where bin is a gene or another specified genomic region comprising the nucleic acid variant and folded MAF is min(MAF, 1−MAF). In some embodiments, the specified genomic region is a region within about $10^1$, $10^2$, $10^3$, $10^4$, $10^5$, $10^6$, $10^7$, $10^8$, $10^9$, or $10^{10}$ base pairs of the nucleic acid variant. In some embodiments, the associated variable of the nucleic acid variant comprises at least one single nucleotide polymorphism (SNP) comprising a population allele frequency (AF) greater than about 0.001. In some embodiments, the associated variable of the nucleic acid variant comprises at least one non-oncogenic single nucleotide polymorphism (SNP). In some embodiments, the associated variable of the nucleic acid variant comprises at least one single nucleotide polymorphism (SNP) comprising a mutant allele fraction (MAF) less than about 0.9.

In some embodiments, the associated variable comprises at least one heterozygous SNP within a specified genomic region relative to the nucleic acid variant, and wherein beta binomial distribution parameters are estimated using: (x, y)~Beta binomial($\mu_{bin}$, ρ), wherein y=a vector of total molecule count of the at least one germline heterozygous SNP, with one entry for each germline heterozygous SNP; x=a vector of min(mutant allele count of the at least one germline heterozygous SNP, y—mutant allele count of the at least one germline heterozygous SNP), with one entry for each germline heterozygous SNP; $\mu_{bin}$=an estimate of the mutant allele count of the heterozygous SNPs in a bin, wherein the bin is the specified genomic region relative to the nucleic acid variant; and ρ=an estimate of a dispersion parameter. In some embodiments, an upper bound and a lower bound for the p-value are calculated. In some embodiments, a two-tailed p-value for the nucleic acid variant is calculated using:

$$p\text{-value}=2*\min(Pr_{bb}(x'>x|\mu_{bin},\rho,B),Pr_{bb}(x'<x|\mu_{bin},\rho,B)),$$

wherein $Pr_{bb}$=a probability of beta binomial; x'=a random variable distributed with the beta binomial; A=a mutant allele count of the nucleic acid variant; and B=a total molecule count of the nucleic acid variant.

In another aspect, the present disclosure provides a method of identifying a somatic or germline origin of a nucleic acid variant from a sample of cell-free deoxyribonucleic acid (cfDNA) molecules, the method comprising: (a) determining a mutant allele count (A) and a total molecule count (B) of the nucleic acid variant from the sample of cfDNA molecules; (b) identifying at least one germline heterozygous single nucleotide polymorphism (SNP) within a specified genomic region relative to the nucleic acid variant; (c) determining a total molecule count (y) and a mutant allele count of the at least one germline heterozygous SNP; (d) calculating a probability value (p-value) for the nucleic acid variant by: (i) determining an estimate of $\mu_{bin}$ and ρ from a beta binomial distribution (x, y)~Beta binomial ($\mu_{bin}$, ρ), wherein y=a vector of total molecule count of the at least one germline heterozygous SNP, with one entry for each germline heterozygous SNP; x=a vector of min (mutant allele count of the at least one germline heterozygous SNP, y—mutant allele count of the at least one germline heterozygous SNP), with one entry for each germline heterozygous SNP; $\mu_{bin}$=an estimate of the mutant allele count of germline heterozygous SNPs in a bin, wherein the bin is the specified genomic region relative to the nucleic acid variant; and ρ=an estimate of a dispersion parameter; (ii) calculating a two-tailed p-value from the below equation:

$$p\text{-value}=2^*\min(Pr_{bb}(x'>A|\mu_{bin},\rho,B),Pr_{bb}(x'<A|\mu_{bin},\rho,B)),$$

wherein $Pr_{bb}$=a probability of beta binomial; x'=a random variable distributed with the beta binomial distribution; A=a mutant allele count of the nucleic acid variant; and B=a total molecule count of the nucleic acid variant; and (e) classifying the nucleic acid variant as (i) being of somatic origin when the p-value is below a predetermined threshold value, or as (ii) being of germline origin when the p-value is at or above the predetermined threshold value.

In some embodiments, ρ comprises a median value of at least one set of ρ values from a historic sample set. In some embodiments, the method comprises determining a maximum likelihood estimate of $\mu_{bin}$. In some embodiments, the method comprises determining a mean estimate of $\mu_{bin}$. In some embodiments, the method comprises determining a maximum likelihood estimate of ρ. In some embodiments, the method comprises determining a variance estimate of ρ. In some embodiments, the method further comprises generating a report in electronic and/or paper format with provides an indication of the classification of the nucleic acid variants as being of either somatic or germline origin.

In another aspect, the present disclosure provides a system, comprising a communication interface that obtains, over a communication network, sequencing information generated from nucleic acids of a sample of nucleic acid molecules (e.g., a sample of cell-free deoxyribonucleic acid (cfDNA) molecules); and a computer in communication with the communication interface, wherein the computer comprises at least one computer processor and a non-transitory computer-readable medium comprising machine-executable code that, upon execution by at least one computer processor, implements a method comprising: (a) determining a plurality of quantitative measures for a nucleic acid variant from the sequencing information, wherein the plurality of quantitative measures comprises a total allele count and a minor allele count for the nucleic acid variant; (b) identifying an associated variable of the nucleic acid variant from the sequencing information; (c) determining a quantitative value for the associated variable of the nucleic acid variant; (d) generating a statistical model for expected germline mutant allele counts at a genomic locus of the nucleic acid variant; (e) generating a probability value (p-value) for the nucleic acid variant based at least in part on the statistical model for expected germline mutant allele counts, the quantitative value for the associated variable of the nucleic acid variant, and at least one of the plurality of quantitative measures for the nucleic acid variant; and (f) classifying the nucleic acid variant as (i) being of somatic origin when the p-value of the nucleic acid variant is below a predetermined threshold value, or as (ii) being of germline origin when the p-value for the nucleic acid variant is at or above the predetermined threshold value.

In some embodiments, the sequencing information is provided by a nucleic acid sequencer. In some embodiments, the nucleic acid sequencer performs pyrosequencing, single-molecule sequencing, nanopore sequencing, semiconductor sequencing, sequencing-by-synthesis, sequencing-by-ligation, or sequencing-by-hybridization of the nucleic acids to generate the sequencing information. In some embodiments, the nucleic acid sequencer uses a clonal single molecule array derived from a sequencing library to generate the sequencing information. In some embodiments, the nucleic acid sequencer comprises a chip having an array of microwells for sequencing a sequencing library to generate the sequencing information. In some embodiments, the non-transitory computer-readable medium comprises a memory, a hard drive, or a memory or a hard drive of a computer server. In some embodiments, the communication network comprises one or more computer servers capable of distributed computing. In some embodiments, the distributed computing is cloud computing. In some embodiments, the computer is part of a computer server that is located at a location remote from the nucleic acid sequencer. In some embodiments, the system further comprises: an electronic display in communication with the computer over a network, wherein the electronic display comprises a user interface for displaying results upon implementing at least a portion of (a)-(f). In some embodiments, the user interface is a graphical user interface (GUI) or web-based user interface. In some embodiments, the electronic display is part of a personal computer. In some embodiments, the electronic display is part of an internet-enabled computer. In some embodiments, the internet-enabled computer is located at a location remote from the computer. In some embodiments, the non-transitory computer-readable medium comprises a memory, a hard drive or a memory or a hard drive of a computer server. In some embodiments, the communication network comprises a telecommunication network, an internet, an extranet, or an intranet.

In another aspect, the present disclosure provides a method of treating a disease in a subject, the method comprising administering one or more customized therapies to the subject, thereby treating the disease in the subject, wherein the customized therapies have been identified by: (a) determining one or more quantitative measures for a nucleic acid variant from a sample of nucleic acid molecules (e.g., a sample of cell-free DNA), wherein the quantitative measures comprise a total allele count and minor allele count for the nucleic acid variant; (b) identifying at least one associated variable of the nucleic acid variant from the sample of nucleic acid molecules; (c) determining a quantitative value for the associated variable of the nucleic acid variant; (d) generating a statistical model for expected germline mutant allele counts at the genomic locus of the nucleic acid variant; (e) generating a probability value (p-value) for the nucleic acid variant based on the statistical model for expected germline allele counts and the quantitative value for the associated variable of the nucleic acid variant and at least one of the quantitative measures for the nucleic acid variant; (f) classifying the nucleic acid variant (i) as being of somatic origin when the p-value of the nucleic acid variant is below a threshold value, or (ii) as being of germline origin when the p-value of the nucleic acid variant is at or above the threshold value; (g) comparing the classified nucleic acid variant to one or more comparator results that are indexed with one or more therapies; and (h) identifying one or more customized therapies for treating the disease in the subject when there is a substantial match between the classified nucleic acid variant and the comparator results.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The accompanying drawings, which are incorporated in and constitute a part of this specification, illustrate certain embodiments, and together with the written description, serve to explain certain principles of the methods, computer readable media, and systems disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DEFINITIONS

Figure 1:
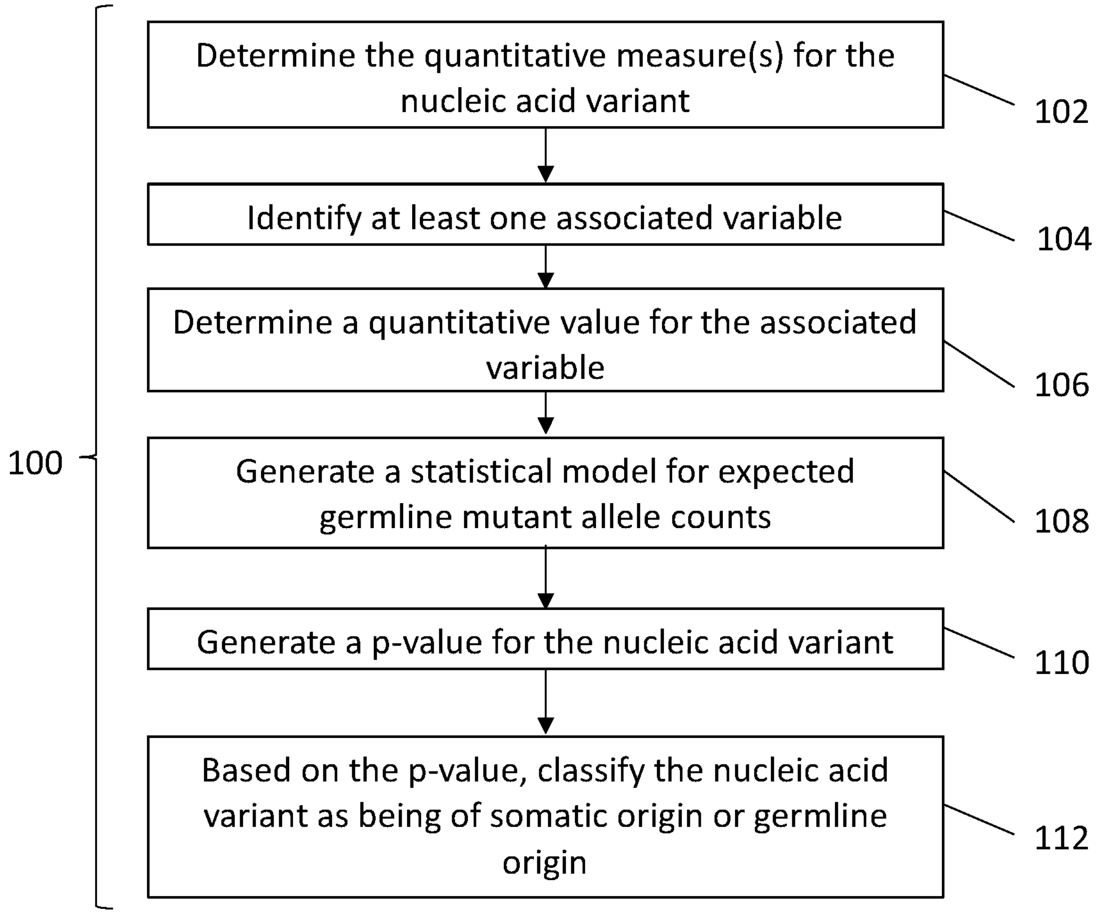
FIG. 1 is a flow chart representation of a method for differentiating somatic and germline variants in a sample of nucleic acid molecules according to an embodiment of the disclosure.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons of ordinary skill in the art upon reading this disclosure and so forth.

It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this disclosure pertains. In describing and claiming the methods, computer readable media, and systems, the following terminology, and grammatical variants thereof, will be used in accordance with the definitions set forth below.

About: As used herein, "about" or "approximately" as applied to one or more values or elements of interest, refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Adapter: As used herein, "adapter" refers to short nucleic acids (e.g., less than about 500 nucleotides, less than about 100 nucleotides, or less than about 50 nucleotides in length) that are typically at least partially double-stranded and used to link to either or both ends of a given sample nucleic acid molecule. Adapters can include nucleic acid primer binding sites to permit amplification of a nucleic acid molecule flanked by adapters at both ends, and/or a sequencing primer binding site, including primer binding sites for sequencing applications, such as various next generation sequencing (NGS) applications. Adapters can also include binding sites for capture probes, such as an oligonucleotide attached to a flow cell support or the like. Adapters can also include a nucleic acid tag as described herein. Nucleic acid tags are typically positioned relative to amplification primer and sequencing primer binding sites, such that a nucleic acid tag is included in amplicons and sequencing reads of a given nucleic acid molecule. The same or different adapters can be linked to the respective ends of a nucleic acid molecule. In some embodiments, the same adapter is linked to the respective ends of the nucleic acid molecule except that the nucleic acid tag differs. In some embodiments, the adapter is a Y-shaped adapter in which one end is blunt ended or tailed as described herein, for joining to a nucleic acid molecule, which is also blunt ended or tailed with one or more complementary nucleotides. In still other example embodiments, an adapter is a bell-shaped adapter that includes a blunt or tailed end for joining to a nucleic acid molecule to be analyzed. Other examples of adapters include T-tailed and C-tailed adapters.

Amplify: As used herein, "amplify" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes.

Associated Variable: As used herein, the term "associated variable" is related to the nucleic acid variant and it refers to a variable that is used in estimating the expected germline mutant allele counts. Such variable can include, but not limited to, germline heterozygous SNP(s), GC content measure, probe-specific bias measure, fragment length value, sequencing statistics measure, copy number breakpoint, clinical data from the subject or any combination thereof.

Cancer Type: As used herein, "cancer type" refers to a type or subtype of cancer defined, e.g., by histopathology. Cancer type can be defined by any conventional criterion, such as on the basis of occurrence in a given tissue (e.g., blood cancers, central nervous system (CNS), brain cancers, lung cancers (small cell and non-small cell), skin cancers, nose cancers, throat cancers, liver cancers, bone cancers, lymphomas, pancreatic cancers, bowel cancers, rectal cancers, thyroid cancers, bladder cancers, kidney cancers, mouth cancers, stomach cancers, breast cancers, prostate cancers, ovarian cancers, lung cancers, intestinal cancers, soft tissue cancers, neuroendocrine cancers, gastroesophageal cancers, head and neck cancers, gynecological cancers, colorectal cancers, urothelial cancers, solid state cancers, heterogeneous cancers, homogenous cancers), unknown primary origin and the like, and/or of the same cell lineage (e.g., carcinoma, sarcoma, lymphoma, cholangiocarcinoma, leukemia, mesothelioma, melanoma, or glioblastoma) and/or cancers exhibiting cancer markers, such as Her2, CA15-3, CA19-9, CA-125, CEA, AFP, PSA, HCG, hormone receptor and NMP-22. Cancers can also be classified by stage (e.g., stage 1, 2, 3, or 4) and whether of primary or secondary origin.

Cell-Free Nucleic Acid: As used herein, "cell-free nucleic acid" refers to nucleic acids not contained within or otherwise bound to a cell or, in some embodiments, nucleic acids remaining in a sample following the removal of intact cells. Cell-free nucleic acids can include, for example, all non-encapsulated nucleic acids sourced from a bodily fluid (e.g., blood, plasma, serum, urine, cerebrospinal fluid (CSF), etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), and/or fragments of any of these. Cell-free nucleic acids can be double-stranded, single-stranded, or a hybrid thereof. A cell-free nucleic acid can be released into bodily fluid through secretion or cell death processes, e.g., cellular necrosis, apoptosis, or the like. Cell-free nucleic acids can be found within an efferosome or an exosome, in cases where the efferosome or exosome has taken up cell-free nucleic acids released from other cells. Some cell-free nucleic acids are released into bodily fluid from cancer cells, e.g., circulating tumor DNA (ctDNA). Others are released from healthy cells. CtDNA can be non-encapsulated tumor-derived fragmented DNA. Another example of cell-free nucleic acids is fetal DNA circulating freely in the maternal blood stream, also called cell-free fetal DNA (cffDNA). A cell-free nucleic acid can have one or more epigenetic modifications, for example, a cell-free nucleic acid can be acetylated, 5-methylated, ubiquitylated, phosphorylated, sumoylated, ribosylated, and/or citrullinated.

Cellular Nucleic Acids: As used herein, "cellular nucleic acids" means nucleic acids that are disposed within one or more cells from which the nucleic acids have originated, at least at the point a sample is taken or collected from a subject, even if those nucleic acids are subsequently removed (e.g., via cell lysis) as part of a given analytical process.

Common Germline Heterozygous SNP: As used herein, the term "common germline heterozygous SNP refers to germline heterozygous single nucleotide polymorphism (SNP) obtained from external population databases (e.g., ExAC) and/or from any historic sample set such that the heterozygous SNPs have at least a particular population allele frequency (AF), wherein the particular population AF can be any value between 0 and 1.

Comparator Result: As used herein, "comparator result" means a result or set of results to which a given test sample or test result can be compared to identify one or more likely properties of the test sample or result, and/or one or more possible prognostic outcomes and/or one or more customized therapies for the subject from whom the test sample was taken or otherwise derived. Comparator results are typically obtained from a set of reference samples (e.g., from subject having the same disease or cancer type as the test subject).

Copy Number Breakpoint: As used herein, the term "copy number breakpoint" refers to a genomic locus at which the copy number (CN) of two neighboring genomic regions (within the same chromosome) on either side of that genomic locus is different.

Copy Number Variant: As used herein, "copy number variant," "CNV," or "copy number variation" refers to a phenomenon in which sections of the genome are repeated and the number of repeats in the genome varies between individuals in the population under consideration and varies between two conditions or states of an individual (e.g., CNV can vary in an individual before and after receiving a therapy).

Coverage: As used herein, the terms "coverage", "total molecule count" or "total allele count" are used interchangeably. They refer to the total number of DNA molecules at a particular genomic position in a given sample.

Customized Therapy: As used herein, "customized therapy" refers to a therapy that is associated with a desired therapeutic outcome for a subject or population of subjects having a given classified nucleic acid variant.

Deoxyribonucleic Acid or Ribonucleic Acid: As used herein, "deoxyribonucleic acid" or "DNA" refers a natural or modified nucleotide which has a hydrogen group at the 2'-position of the sugar moiety. DNA typically includes a chain of nucleotides comprising four types of nucleotides; adenine (A), thymine (T), cytosine (C), and guanine (G). As used herein, "ribonucleic acid" or "RNA" refers to a natural or modified nucleotide which has a hydroxyl group at the 2'-position of the sugar moiety. RNA typically includes a chain of nucleotides comprising four types of nucleotides; A, uracil (U), G, and C. As used herein, the term "nucleotide" refers to a natural nucleotide or a modified nucleotide. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data", "nucleic acid sequencing information", "sequence information", "nucleic acid sequence", "nucleotide sequence", "genomic sequence", "genetic sequence", or "fragment sequence", or "nucleic acid sequencing read" denotes any information or data that is indicative of the order and identity of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

Expected Germline Mutant Allele Count: As used herein, the term "expected germline mutant allele counts" refers to the expected mutant allele counts of a germline SNP at the genomic locus of the nucleic acid variant. For example, the expected germline mutant allele counts can be estimated by a statistical distribution. The statistical distribution can be, but not limited to, beta binomial distribution. The distribution is used to determine the mutant allele count that we expect in a germline heterozygous SNP at that locus. For example, if a beta binomial distribution is used to determine the expected germline mutant allele counts at a particular genomic locus, then the distribution of the expected mutant allele count is parameterized by the mean estimate ($\mu$), dispersion estimate ($\rho$) and coverage at that genomic locus.

Germline Mutation: As used herein, the terms "germline mutation" or "germline variation" are used interchangeably and refer to an inherited mutation (i.e., not one arising post-conception). Germline mutations may be the only mutations that can be passed on to the offspring and may be present in every somatic cell and germline cell in the offspring.

Historic Sample Set: As used herein, the term "historic sample set" refers to a set of samples which are obtained from normal subjects (having no disease/cancer), subjects having any disease or cancer, subjects having a particular cancer type and/or subjects who are receiving or have received a particular therapy.

Indel: As used herein, "indel" refers to a mutation that involves the insertion or deletion of nucleotides in the genome of a subject.

Mutant Allele Count: As used herein, the term "mutant allele count" refers to the number of DNA molecules harboring the mutant allele at a particular genomic locus Minor Allele Count: As used herein, "minor allele count" refers to a number of minor alleles (e.g., not the most common allele) occurring in a given population of nucleic acids, such as a sample obtained from a subject. Genetic variants at a low minor allele count typically have a relatively low number present in a sample.

Mutant Allele Fraction: As used herein, "mutant allele fraction", "mutation dose," or "MAF" refers to the fraction of nucleic acid molecules harboring an allelic alteration or mutation at a given genomic position/locus in a given sample. MAF is generally expressed as a fraction or a percentage. For example, an MAF of a somatic variant may be less than 0.15.

Mutation: As used herein, "mutation" refers to a variation from a known reference sequence and includes mutations such as, for example, single nucleotide variants (SNVs), and insertions or deletions (indels). A mutation can be a germline or somatic mutation. In some embodiments, a reference sequence for purposes of comparison is a wildtype genomic sequence of the species of the subject providing a test sample, typically the human genome.

Mutation Caller: As used herein, "mutation caller" means an algorithm (typically, embodied in software or otherwise computer implemented) that is used to identify mutations in test sample data (e.g., sequence information obtained from a subject).

Neoplasm: As used herein, the terms "neoplasm" and "tumor" are used interchangeably. They refer to abnormal growth of cells in a subject. A neoplasm or tumor can be benign, potentially malignant, or malignant. A malignant tumor is a referred to as a cancer or a cancerous tumor.

Next Generation Sequencing: As used herein, "next generation sequencing" or "NGS" refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

Nucleic Acid Tag: As used herein, "nucleic acid tag" refers to a short nucleic acid (e.g., less than about 500 nucleotides, about 100 nucleotides, about 50 nucleotides, or about 10 nucleotides in length), used to distinguish nucleic acids from different samples (e.g., representing a sample index), or different nucleic acid molecules in the same sample (e.g., representing a molecular barcode), of different types, or which have undergone different processing. Such nucleic acid tags may be used to label different nucleic acid molecules or different nucleic acid samples or sub-samples. Nucleic acid tags can be single stranded, double stranded or at least partially double-stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or to both ends of the other nucleic acids (e.g., sample nucleic acids to be amplified and/or sequenced). Nucleic acid tags can be decoded to reveal information such as the sample of origin, form or processing of a given nucleic acid. For example, nucleic acid tags can also be used to enable pooling and/or parallel processing of multiple samples comprising nucleic acids bearing different molecular barcodes and/or sample indexes in which the nucleic acids are subsequently being deconvolved by detecting (e.g., reading) the nucleic acid tags. Nucleic acid tags can also be referred to as identifiers or indexes. Such nucleic acid tags, identifiers, or indexes may comprise one or more barcodes. Additionally, or alternatively, nucleic acid tags can be used as molecular identifiers or indexes (e.g., to distinguish between different molecules or amplicons of different parent molecules in the same sample or sub-sample). This includes, for example, uniquely tagging each different nucleic acid molecule in a given sample, or non-uniquely tagging such molecules. In the case of non-unique tagging applications, a limited number of tags (e.g., barcodes) may be used to tag each nucleic acid molecule such that different molecules can be distinguished based on their endogenous sequence information (for example, start and/or stop positions where they map to a selected reference genome, a sub-sequence of one or both ends of a sequence, and/or length of a sequence) in combination with at least one barcode. Typically, a sufficient number of different nucleic acid tags are used such that there is a low probability (e.g., less than about a 10%, less than about a 5%, less than about a 1%, or less than about a 0.1% chance) that any two molecules may have the same endogenous sequence information (e.g., start and/or stop positions, subsequences of one or both ends of a sequence, and/or lengths) and also have the same nucleic acid tag (e.g., barcode). Alternatively, nucleic acid tags may comprise only endogenous sequence information (e.g., start and/or stop positions, sub-sequences of one or both ends of a sequence, and/or lengths). Some nucleic acid tags include multiple molecular identifiers to label samples, forms of nucleic acid molecules within a sample, and nucleic acid molecules within a form having the same endogenous sequence information (e.g., start and/or stop positions, sub-sequences of one or both ends of a sequence, and/or lengths). Such nucleic acid tags can be referenced using the example form "A1i" in which the uppercase letter indicates a sample type, the Arabic numeral indicates a form of molecule within a sample, and the lowercase Roman numeral indicates a molecule within a form.

Polynucleotide: As used herein, "polynucleotide", "nucleic acid", "nucleic acid molecule", or "oligonucleotide" refers to a linear polymer of nucleosides (including deoxyribonucleosides, ribonucleosides, or analogs thereof) joined by inter-nucleosidic linkages. Typically, a polynucleotide comprises at least three nucleosides. Oligonucleotides often range in size from a few monomeric units, e.g., 3-4, to hundreds of monomeric units. Whenever a polynucleotide is represented by a sequence of letters, such as "ATGCCTG", it will be understood that the nucleotides are in 5→3' order from left to right and that in the case of DNA, "A" denotes deoxyadenosine, "C" denotes deoxycytidine, "G" denotes deoxyguanosine, and "T" denotes deoxythymidine, unless otherwise noted. The letters A, C, G, and T may be used to refer to the bases themselves, to nucleosides, or to nucleotides comprising the bases, as is standard in the art.

Reference Sequence: As used herein, "reference sequence" refers to a known sequence used for purposes of comparison with experimentally determined sequences. For example, a known sequence can be an entire genome, a chromosome, or any segment thereof. A reference typically includes at least about 20, at least about 50, at least about 100, at least about 200, at least about 250, at least about 300, at least about 350, at least about 400, at least about 450, at least about 500, at least about 1000, or more than 1000 nucleotides. A reference sequence can align with a single contiguous sequence of a genome or chromosome or can include non-contiguous segments that align with different regions of a genome or chromosome. Examples of reference sequences include, for example, human genomes, such as, hG19 and hG38.

Sample: As used herein, "sample" means anything capable of being analyzed by the methods and/or systems disclosed herein.

Sequencing: As used herein, "sequencing" refers to any of a number of technologies used to determine the sequence (e.g., the identity and order of monomer units) of a biomolecule, e.g., a nucleic acid such as DNA or RNA. Examples of sequencing methods include, but are not limited to, targeted sequencing, single molecule real-time sequencing, exon or exome sequencing, intron sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performer by a gene analyzer such as, for example, gene analyzers commercially available from Illumina, Inc., Pacific Biosciences, Inc., or Applied Biosystems/Thermo Fisher Scientific, among many others.

Sequence Information: As used herein, "sequence information" in the context of a nucleic acid polymer means the order and identity of monomer units (e.g., nucleotides, etc.) in that polymer.

Single Nucleotide Polymorphism: As used herein, the terms "single nucleotide polymorphism" or "SNP" are used interchangeably. They refer to a variation in a single nucleotide that occurs at a specific position in the genome, where each variation is present to some appreciable degree within a population (e.g., greater than about 1%)

Single Nucleotide Variant: As used herein, "single nucleotide variant" or "SNV" means a mutation or variation in a single nucleotide that occurs at a specific position in the genome.

Somatic Mutation: As used herein, the terms "somatic mutation" or "somatic variation" are used interchangeably. They refer to a mutation in the genome that occurs after conception. Somatic mutations can occur in any cell of the body except germ cells and accordingly, are not passed on to progeny.

Subject: As used herein, "subject" refers to an animal, such as a mammalian species (e.g., human) or avian (e.g., bird) species, or other organism, such as a plant. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual in need of therapy or suspected of needing therapy. The terms "individual" or "patient" are intended to be interchangeable with "subject."

For example, a subject can be an individual who has been diagnosed with having a cancer, is going to receive a cancer therapy, and/or has received at least one cancer therapy. The subject can be in remission of a cancer. As another example, the subject can be an individual who is diagnosed of having an autoimmune disease. As another example, the subject can be a female individual who is pregnant or who is planning on getting pregnant, who may have been diagnosed of or suspected of having a disease, e.g., a cancer, an autoimmune disease.

Substantial Match: As used herein, "substantial match" means that at least a first value or element is at least approximately equal to at least a second value or element. In certain embodiments, for example, customized therapies are identified when there is at least a substantial or approximate match between a classified nucleic acid variant and a comparator result.

Threshold: As used herein, "threshold" refers to a predetermined value used to characterize experimentally determined values of the same parameter for different samples depending on their relation to the threshold. For example, the threshold for the p-value can refer to any predetermined value between 0 and 1 and is used to identify the origin of a nucleic acid variant.

Variant: As used herein, a "variant" can be referred to as an allele. A variant is usually presented at a frequency of 50% (0.5) or 100% (1), depending on whether the allele is heterozygous or homozygous. For example, germline variants are inherited and usually have a frequency of 0.5 or 1. Somatic variants, however, are acquired variants and usually have a frequency of less than about 0.5. Major and minor alleles of a genetic locus refer to nucleic acids harboring the locus in which the locus is occupied by a nucleotide of a reference sequence, and a variant nucleotide different than the reference sequence respectively. Measurements at a locus can take the form of allelic fractions (AFs), which measure the frequency with which an allele is observed in a sample.

DETAILED DESCRIPTION

I. Overview

The present disclosure provides methods and systems for using a statistical model, such as a beta binomial model, for classifying or identifying a nucleic acid variant in a sample of nucleic acid molecules as being of somatic or germline origin. In some embodiments, the methods and systems of the present disclosure are suitable for analyzing cell-free nucleic acids, such as cell-free DNA (cfDNA). Many solutions available for differentiating somatic variants and germline variants using sequencing data from tumor tissues may rely on the availability of matched pairs of tumor and normal tissues and thus may not be applied to data obtained from cell-free nucleic acids. Solutions for analyzing cfDNA samples may include thresholding on the mutant allele fraction (MAF) or applying a Poisson statistical model to determine germline or somatic status. However, such approaches may not accurately model the variance seen in cfDNA molecule counts and hence the somatic/germline differentiation based on these approaches may not be optimally accurate. The methods and systems disclosed herein can accurately model the variance seen in nucleic acid molecule counts (such as in cfDNA) and can differentiate somatic and germline variants with high accuracy. The methods and systems disclosed herein can use parameters, such as common germline single nucleotide polymorphisms (SNPs), to statistically model local germline mutant allele count behavior (e.g., the germline mutant allele count behavior in the genomic region relative to the nucleic acid variant), and distinguish somatic variants based on MAF deviation from the observed germline MAF.

In an aspect, the present disclosure provides a method for identifying a somatic or germline origin of a nucleic acid variant from a cell-free deoxyribonucleic acid (cfDNA) sample, comprising: (a) determining a plurality of quantitative measures for the nucleic acid variant from the cfDNA sample, wherein the plurality of quantitative measures comprises a total allele count and a minor allele count for the nucleic acid variant; (b) identifying an associated variable of the nucleic acid variant from the cfDNA sample; (c) determining a quantitative value for the associated variable of the nucleic acid variant; (d) generating a statistical model for expected germline mutant allele counts at a genomic locus of the nucleic acid variant; (e) generating a probability value (p-value) for the nucleic acid variant based at least in part on the statistical model for expected germline mutant allele counts, the quantitative value for the associated variable of the nucleic acid variant, and at least one of the plurality of quantitative measures for the nucleic acid variant; and (f) classifying the nucleic acid variant as (i) being of somatic origin when the p-value for the nucleic acid variant is below a predetermined threshold value, or as (ii) being of germline origin when the p-value for the nucleic acid variant is at or above the predetermined threshold value.

FIG. 1 illustrates an example embodiment of a method 100 for differentiating somatic and germline variants in a sample of nucleic acid molecules. Once a nucleic acid variant is identified from the nucleic acid molecules in the sample, quantitative values relating to the nucleic acid variant and associated variables may be established to provide input values for implementing the statistical model. Nucleic acid variants may be identified or detected by any known method, including, but not limited to methods described in U.S. Pat. Nos. 9,598,731, 9,834,822, 9,840,743, and 9,902,992 each of which is hereby incorporated by reference in its entirety.

In operation 102, quantitative values for the nucleic acid variant may be measured and determined. These values may include, but are not limited to, a mutant allele count and/or a total molecule count of the nucleic acid variant.

Another input value required for the model may be the quantitative value(s) for the associated variable(s). In operation 104, at least one associated variable may be identified. The associated variables may be used in estimating the expected germline mutant allele counts at the genomic locus of the nucleic acid variant. Such associated variables may include, but are not limited to, germline heterozygous SNP(s), GC content measure, probe-specific bias measure, fragment length value, sequencing statistics measure, copy number breakpoint, clinical data from the subject, or any combination thereof.

In some embodiments, the associated variable can be within a specified genomic region (also referred to as a "bin") relative to the nucleic acid variant. In some embodiments, the bin may be a gene comprising the nucleic acid variant. In some embodiments, the bin can be a specified genomic region relative to the nucleic acid variant. In some embodiments, the bin (specified genomic region) is within about $10^1$, $10^2$, $10^3$, $10^4$, $10^5$, $10^6$, $10^7$, $10^8$, $10^9$, $10^{10}$, or more than $10^{10}$ bases of the nucleic acid variant. In some embodiments, the bin is within 'N' bases of the nucleic acid variant, where N is about 1, about 5, about 10, about 25, about 50, about 100, about 250, about 500, about 1 thousand, about 5 thousand, about 10 thousand, about 50 thousand, about 100 thousand, about 500 thousand, about 1 million, or more than about 1 million bases. In some embodiments, N can be up to 300 million bases. For example, the bin can be within $10^5$ bases of the nucleic acid variant. In some embodiments, the associated variable of the nucleic acid variant comprises a genomic locus that is linked to a genomic locus that comprises the nucleic acid variant. In some embodiments, the associated variable can comprise at least one, at least two, at least five, at least ten, or more than ten heterozygous SNPs. In some embodiments, the associated variable of the nucleic acid variant comprises at least one SNP comprising a population allele frequency (AF) of at least 0.00001, at least 0.0001, at least 0.001, at least 0.002, at least 0.005, at least 0.01, at least 0.02, at least 0.05, at least 0.1, at least 0.2, at least 0.5, at least 0.75, or at least 0.99. In some embodiments, the associated variable of the nucleic acid variant comprises at least one SNP comprising a population allele frequency (AF) value between 0 and 1. In some embodiments, the associated variable of the nucleic acid variant comprises at least one single nucleotide polymorphism (SNP) comprising a mutant allele fraction (MAF) less than 0.9. In some embodiments, the associated variable of the nucleic acid variant comprises at least one single nucleotide polymorphism (SNP) comprising a mutant allele fraction (MAF) between 0 and about 1. In some embodiments, the associated variable of the nucleic acid variant comprises at least one heterozygous SNP, wherein the heterozygous SNP can be a common germline heterozygous SNP.

In some embodiments, the associated variable is within a copy number breakpoint. Instead of having fixed-width bins or bins defined by gene annotation, the associated variable may be identified in bins that are delineated by copy number breakpoints, so that each nucleic acid variant's bin is as wide as possible without overlapping any copy number breakpoints. In some embodiments, the associated variable comprises heterozygous SNPs within a copy number breakpoint.

In operation 106, the quantitative value(s) for the associated variable(s) of the nucleic acid variant may be determined. The quantitative value of the associated variable may be used as an input in applying the statistical model to estimate the expected germline mutant allele counts at the genomic locus of the nucleic acid variant. In some embodiments, the quantitative value for the associated variable comprises a mutant allele count and/or a total molecule count of the associated variable. In some embodiments, the method further comprises determining a MAF. In some embodiments, the MAF is adjusted to a reduced scale, referred to herein as a "folded MAF" of the associated variable, wherein the folded MAF=min (MAF, 1−MAF). In some embodiments, the method comprises determining a folded mutant allele count of the associated variable, wherein the folded mutant allele count=min (mutant allele count, total molecule count−mutant allele count). In some embodiments, the quantitative value can comprise one or more allele counts identified at the associated variable of the nucleic acid variant. In some embodiments, the method comprises determining a mean and/or a variance value of one or more allele counts identified at the associated variable of the nucleic acid variant. In some embodiments, the method comprises determining an average quantitative value for the associated variable of the nucleic acid variant. In some embodiments, the method comprises determining a mean and/or a variance value of the associated variable of the nucleic acid variant. In some embodiments, the associated variable of the nucleic acid variant comprises at least one non-oncogenic SNP.

In operation 108, the determined quantitative values may be processed using a statistical model, such as a beta binomial model. The distribution generated from the statistical model may be used to determine the mutant allele count that may be expected in a germline heterozygous SNP at that locus. For example, if a beta binomial distribution is used to determine the expected germline mutant allele counts at a particular genomic locus, then the distribution of the expected germline mutant allele count may be parameterized by a set of statistical parameters corresponding to the beta binomial distribution, e.g., the mean estimate (μ), dispersion estimate (ρ), and coverage at that genomic locus. In some embodiments, the method comprises determining $\mu_{bin}$ for the nucleic acid variant, wherein $\mu_{bin}$ is an estimate of the mutant allele count of the heterozygous SNP(s) in a bin.

In some embodiments, the associated variable comprises at least one heterozygous single nucleotide polymorphism (SNP) within a specified genomic region relative to the nucleic acid variant, and the method comprises estimating beta binomial distribution parameters using:

$$(x, y) \sim \text{Beta binomial}(\mu_{bin}, \rho),$$

where y=a vector of total molecule count of the germline heterozygous SNP, with one entry for each germline heterozygous SNP considered; x=a vector of min(mutant allele count of the germline heterozygous SNP, y—mutant allele count of the germline heterozygous SNP), with one entry for each germline heterozygous SNP considered; $\mu_{bin}$=an estimate of the mutant allele count of heterozygous SNPs in a bin, wherein the bin is a specified genomic region relative to the nucleic acid variant; and ρ=an estimate of the dispersion parameter.

In certain embodiments, x and y may be represented as vectors with one entry for each germline heterozygous SNP. This may be the case if two or more germline heterozygous SNPs are considered in the model. For example, if two germline heterozygous SNPs are considered, then y will be represented as a vector of $y_1$ (total molecule count for het $SNP_1$) and $y_2$ (total molecule count for het $SNP_2$). Likewise, x will be represented as a vector of $x_1$ (for het $SNP_1$) and $x_2$ (for het $SNP_2$). In some embodiments, only one germline heterozygous SNP may be considered. In these cases, the values for x and y may be represented as vectors with only one entry or, alternatively, as y=a total molecule count of the heterozygous SNP and x=min (mutant allele count of the heterozygous SNP, y—mutant allele count of the heterozygous SNP).

In some embodiments, the ρ comprises a median value of at least one set of ρ values from a historic sample set. In some embodiments, the method comprises replacing the median ρ parameter with a function of GC content of nucleic acid variant. In some embodiments, the method comprises determining a maximum likelihood estimate of $\mu_{bin}$. In some embodiments, the method determining a mean estimate of $\mu_{bin}$. In some embodiments, the method comprises determining a maximum likelihood estimate of ρ. In some embodiments, the method comprises determining a variance estimate of ρ.

In some embodiments, rather than being modeled as a fixed number, the dispersion parameter (ρ) can be modeled as a function of the GC content of the local genomic context (e.g., genomic context of a bin). The function can be estimated from a historic sample set, and the median value of ρ in the above equation can be replaced by the value of this function at the variant's GC content level.

In operation 110, a probability value (p-value) for the nucleic acid variant may be determined based at least in part on the statistical model for expected germline mutant allele counts, the quantitative value for the associated variable of the nucleic acid variant, and at least one of the quantitative measures for the nucleic acid variant. In some embodiments, the method comprises calculating a two-tailed p-value for the nucleic acid variant using:

$$p-\text{value}=2*\min(Pr_{bb}(x'>A\mid\mu_{bin},\rho,B),\,Pr_{bb}(x'<A\mid\mu_{bin},\rho,B))$$

where $Pr_{bb}$=a probability of beta binomial; x'=a random variable distributed with the beta binomial; A=a mutant allele count of the nucleic acid variant; and B=a total molecule count of the nucleic acid variant.

In operation 112, the nucleic acid variant may be classified as (i) being of somatic origin when the p-value of the nucleic acid variant is below a threshold value, or (ii) being of germline origin when the p-value of the nucleic acid variant is at or above the threshold value. The threshold value can be any value that can differentiate germline variants and somatic variants. The threshold value can be determined from empirical data. For example, the threshold value can be any value between 0 and 1. In some embodiments, the threshold value can be at least $10^{-50}$, at least $10^{-40}$, at least $10^{-30}$, at least $10^{-20}$, at least $10^{-10}$, at least $10^{-5}$, at least 0.01, at least 0.01, at least 0.1, at least 0.2, at least 0.5, at least 0.75, or at least 0.99. In some embodiments, the method comprises generating the threshold value using a beta-binomial model of expected germline mutant allele counts for nucleic acids in the sample.

In some embodiments, the method comprises classifying the somatic or germline origin of multiple nucleic acid variants from a plurality of genomic loci in the nucleic acid sample.

The methods and systems disclosed herein generally include obtaining sequence information from nucleic acids in samples taken from subjects. In some embodiments, the method further comprises receiving sequencing information generated from the nucleic acid sample, wherein the sequencing information comprises sequencing reads from the nucleic acid variant and nucleic acids comprising the associated variable of the nucleic acid variant, which associated variable comprises at least one heterozygous single nucleotide polymorphism (SNP) within a specified genomic region relative to the nucleic acid variant. In some embodiments, the method further comprises sequencing nucleic acids from the sample to generate sequencing information, wherein the quantitative measures are determined from the sequencing information. In some embodiments, the method comprises determining quantitative measures for the nucleic acid variant, identifying the associated variable of the nucleic acid variant, and determining a quantitative value from sequencing information generated from the sample.

In another aspect, the present disclosure provides a method of identifying a somatic or germline origin of a nucleic acid variant from a sample of cell-free nucleic acids, such as cfDNA, the method comprising: (a) determining a mutant allele count (A) and total molecule count (B) of the nucleic acid variant from the cfDNA sample; (b) identifying at least one germline heterozygous single nucleotide polymorphism (SNP) within a specified genomic region relative to the nucleic acid variant; (c) determining a total molecule count (y) and mutant allele count of the germline heterozygous SNP; (d) calculating a probability value (p-value) comprising: (i) determining an estimate of $\mu_{bin}$ and ρ from a beta binomial distribution given by:

$$(x,y)\sim\text{Beta binomial}(\mu_{bin},\rho),$$

where y=a vector of total molecule count of the at least one germline heterozygous SNP, with one entry for each germline heterozygous SNP considered; x=a vector of min(mutant allele count of the at least one germline heterozygous SNP, y—mutant allele count of the at least one germline heterozygous SNP), with one entry for each germline heterozygous SNP considered; $\mu_{bin}$=an estimate of the mutant allele count of the germline heterozygous SNP(s) in a bin, wherein the bin is a specified genomic region relative to the nucleic acid variant; and ρ=an estimate of the dispersion parameter; (ii) calculating a two-tailed p-value using:

$$p-\text{value}=2*\min(Pr_{bb}(x'>A\mid\mu_{bin},\rho,B),\,Pr_{bb}(x'<A\mid\mu_{bin},\rho,B)),$$

where $Pr_{bb}$=a probability of beta binomial; x'=a random variable distributed with the beta binomial distribution; B=a total molecule count of the nucleic acid variant; and A=a mutant allele count of the nucleic acid variant; (e) classifying the nucleic acid variant as (i) being of somatic origin when the p-value is below a predetermined threshold value, or as (ii) being of germline origin when the p-value is at or above the predetermined threshold value.

In some embodiments, the ρ comprises a median value of at least one set of ρ values from a historic sample set. In some embodiments, the method comprises determining a maximum likelihood estimate of $\mu_{bin}$. In some embodiments, the method comprises determining a mean estimate of $\mu_{bin}$. In some embodiments, the method comprises determining a maximum likelihood estimate of ρ. In some embodiments, the method comprises determining a variance estimate of ρ.

Figure 2:
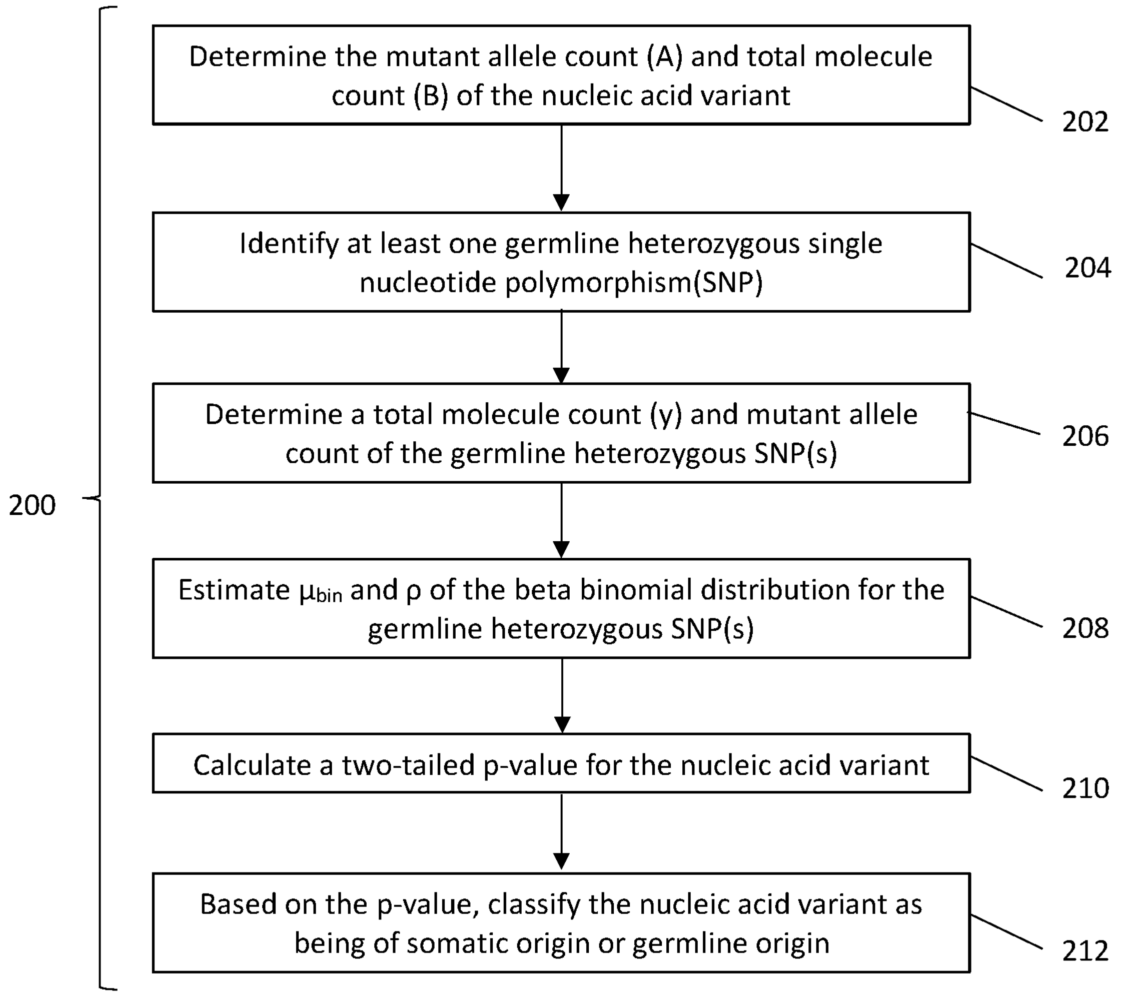
FIG. 2 is a flow chart representation of a method for differentiating somatic and germline variants in a sample of nucleic acid molecules using a beta binomial distribution according to an embodiment of the disclosure.

FIG. 2 illustrates an embodiment of a method for differentiating somatic and germline variants in a sample of cfDNA using a beta binomial model. In operation 202, a mutant allele count (A) and total molecule count (B) of the nucleic acid variant from the cfDNA sample are determined. In operation 204, at least one germline heterozygous single nucleotide polymorphism (SNP) within a specified genomic region relative to the nucleic acid variant may be identified. In operation 206, a total molecule count (y) and mutant allele count of the germline heterozygous SNP(s) may be determined. In operation 208, $\mu_{bin}$ and ρ from a beta binomial distribution may be estimated using $$(x,y)\sim\text{Beta binomial}(\mu_{bin},\rho),$$

where y=a vector of total molecule count of the at least one germline heterozygous SNP, with one entry for each germline heterozygous SNP considered; x=a vector of min(mutant allele count of the at least one germline heterozygous SNP, y—mutant allele count of the at least one germline heterozygous SNP), with one entry for each germline heterozygous SNP considered; $\mu_{bin}$=an estimate of the mutant allele count of the germline heterozygous SNP(s) in a bin, wherein the bin is a specified genomic region relative to the nucleic acid variant; and ρ=an estimate of the dispersion parameter. In operation 210, a two-tailed p-value may be calculated using:

$$p-\text{value}=2*\min(Pr_{bb}(x'>A\mid\mu_{bin},\rho,B),\ Pr_{bb}(x'<A\mid\mu_{bin},\rho,B));$$

where, $Pr_{bb}$=a probability of beta binomial; x'=a random variable distributed with the beta binomial distribution; B=a total molecule count of the nucleic acid variant; and A=a mutant allele count of the nucleic acid variant.

Current solutions for identifying the somatic or germline origin of a variant in cfDNA may include thresholding on the mutant allele fraction (MAF) or applying a Poisson statistical model to determine germline or somatic status. However, such approaches may experience challenges in accurately modeling the variance seen in cfDNA sequencing molecule counts, thus resulting in an inaccurate germline/somatic distinction. Further, these methods may not adjust their somatic-call threshold in response to evidence from nearby variants or other covariates relative to the nucleic acid variant. The beta binomial model may overcome these issues by modeling the distribution of the expected germline mutant allele counts using mean and dispersion estimates and a coverage at the genomic locus of the nucleic acid variant. The mean estimate and dispersion estimates of the expected germline heterozygous SNP may be used in calculating a p-value of the nucleic acid variant, which in turn may be used to classify the variant as of somatic or germline origin.

In operation 212, the nucleic acid variant may be classified as (i) being of somatic origin when the p-value is below a predetermined threshold value, or as (ii) being of germline origin when the p-value is at or above the predetermined threshold value.

Figure 3:
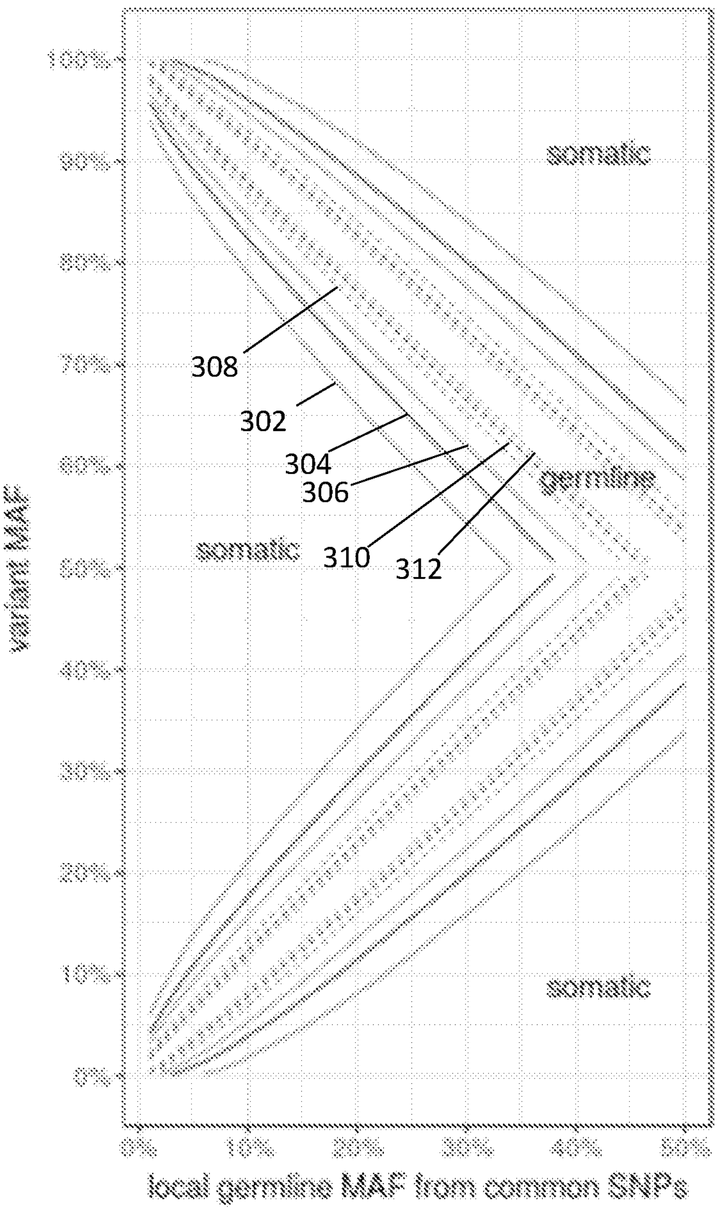
FIG. 3 is a graphical representation of the decision boundary for differentiating germline/somatic variants using a beta binomial distribution.

FIG. 3 shows an example of a decision boundary for differentiating germline/somatic variants using a beta binomial distribution. The beta binomial decision boundary for nucleic acid variant MAF may be a function of MAFs of germline heterozygous SNPs, the total count of molecules observed at the variant position, and an adjustable p-value threshold. As an example, a gene with allele imbalance due to copy number variation (CNV) or loss of heterozygosity (LOH) may have germline MAFs in both the 10-30% and 70-90% ranges. Referring back to FIG. 3, 302 (outer solid line), 304 (middle solid line), and 306 (inner solid line) represent the decision boundary for germline/somatic differentiation using a beta binomial model with a threshold of $10^{-16}$ for the p-value and a variant total molecule count (B) of 700, 1500, and 3000, respectively. Further, 308 (outer broken line), 310 (middle broken line) and 312 (inner broken line) represent the decision boundary for germline/somatic differentiation using a beta binomial model with a threshold of 0.01 for the p-value and a variant total molecule count (B) of 700, 1500, and 3000, respectively.

In some embodiments, the sequence information is obtained from targeted segments of the nucleic acids. Essentially any number of genomic regions may be optionally targeted. The targeted segments can include at least 10, at least 50, at least 100, at least 500, at least 1000, at least 2000, at least 5000, at least 10,000, at least 20,000, at least 50,000, or at least 100,000 (e.g., 25, 50, 75, 100, 200, 300, 400, 500, 600, 700, 800, 900, 1,000, 2,000, 3,000, 4,000, 5,000, 6,000, 7,000, 8,000, 9,000, 10,000, 15,000, 25,000, 30,000, 35,000, 40,000, 45,000, 50,000, or 100,000) different and/or overlapping genomic regions.

In some embodiments, the identified germline and/or somatic variants are used as an input to generate a report in an electronic and/or paper format which provides an indication of the classification of these genetic variants in the polynucleotide as being of either somatic or germline origin.

The various steps of the methods may be carried out at the same or different times, in the same or different geographical locations, e.g. countries, and by the same or different people or entities.

II. General Features of the Methods

A. Samples

A sample can be any biological sample isolated from a subject. Samples can include body tissues, whole blood, platelets, serum, plasma, stool, red blood cells, white blood cells or leucocytes, endothelial cells, tissue biopsies (e.g., biopsies from known or suspected solid tumors), cerebrospinal fluid, synovial fluid, lymphatic fluid, ascites fluid, interstitial or extracellular fluid (e.g., fluid from intercellular spaces), gingival fluid, crevicular fluid, bone marrow, pleural effusions, cerebrospinal fluid, saliva, mucous, sputum, semen, sweat, and urine. Samples may be bodily fluids, such as blood and fractions thereof, and urine. Such samples can include nucleic acids shed from tumors. The nucleic acids can include DNA and RNA and can be in double and single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a bodily fluid for analysis can be plasma or serum containing cell-free nucleic acids, e.g., cell-free DNA (cfDNA).

In some embodiments, the sample volume of bodily fluid taken from a subject depends on the desired read depth for sequenced regions. Examples of volumes are about 0.4-40 milliliters (mL), about 5-20 mL, about 10-20 mL. For example, the volume can be about 0.5 mL, about 1 mL, about 5 mL, about 10 mL, about 20 mL, about 30 mL, about 40 mL, or more milliliters. A volume of sampled plasma is typically between about 5 mL to about 20 mL.

The sample can comprise various amounts of nucleic acid. Typically, the amount of nucleic acid in a given sample is equates with multiple genome equivalents. For example, a sample of about 30 nanograms (ng) DNA can contain about 10,000 ($10^4$) haploid human genome equivalents and, in the case of cfDNA, about 200 billion ($2\times10^{11}$) individual polynucleotide molecules. Similarly, a sample of about 100 ng of DNA can contain about 30,000 haploid human genome equivalents and, in the case of cfDNA, about 600 billion individual molecules.

In some embodiments, a sample comprises nucleic acids from different sources, e.g., from cells and from cell-free sources (e.g., blood samples, etc.). Typically, a sample includes nucleic acids carrying mutations. For example, a sample optionally comprises DNA carrying germline mutations and/or somatic mutations. Typically, a sample comprises DNA carrying cancer-associated mutations (e.g., cancer-associated somatic mutations).

Example amounts of cell-free nucleic acids in a sample before amplification typically range from about 1 femtogram (fg) to about 1 microgram (μg), e.g., about 1 picogram (pg) to about 200 nanograms (ng), about 1 ng to about 100 ng, about 10 ng to about 1000 ng. In some embodiments, a sample includes up to about 600 ng, up to about 500 ng, up to about 400 ng, up to about 300 ng, up to about 200 ng, up to about 100 ng, up to about 50 ng, or up to about 20 ng of cell-free nucleic acid molecules. Optionally, the amount is at least about 1 fg, at least about 10 fg, at least about 100 fg, at least about 1 pg, at least about 10 pg, at least about 100 pg, at least about 1 ng, at least about 10 ng, at least about 100 ng, at least about 150 ng, or at least about 200 ng of cell-free nucleic acid molecules. In some embodiments, the amount is up to about 1 fg, about 10 fg, about 100 fg, about 1 pg, about 10 pg, about 100 pg, about 1 ng, about 10 ng, about 100 ng, about 150 ng, or about 200 ng of cell-free nucleic acid molecules. In some embodiments, methods include obtaining between about 1 fg to about 200 ng cell-free nucleic acid molecules from samples.

Cell-free nucleic acids typically have a size distribution of between about 100 nucleotides in length and about 500 nucleotides in length, with molecules of about 110 nucleotides in length to about 230 nucleotides in length representing about 90% of molecules in the sample, with a mode of about 168 nucleotides length (in samples from human subjects) and a second minor peak in a range between about 240 nucleotides to about 440 nucleotides in length. In some embodiments, cell-free nucleic acids are from about 160 nucleotides to about 180 nucleotides in length, or from about 320 nucleotides to about 360 nucleotides in length, or from about 440 nucleotides to about 480 nucleotides in length.

In some embodiments, cell-free nucleic acids are isolated from bodily fluids through a partitioning step in which cell-free nucleic acids, as found in solution, are separated from intact cells and other non-soluble components of the bodily fluid. In some embodiments, partitioning includes techniques such as centrifugation or filtration. Alternatively, cells in bodily fluids may be lysed, and cell-free and cellular nucleic acids may be processed together. Generally, after addition of buffers and wash steps, cell-free nucleic acids may be precipitated with, for example, an alcohol. In some embodiments, additional clean-up steps are used, such as silica-based columns to remove contaminants or salts. Non-specific bulk carrier nucleic acids, for example, are optionally added throughout the reaction to optimize aspects of the example procedure, such as yield. After such processing, samples typically include various forms of nucleic acids including double-stranded DNA, single-stranded DNA and/or single-stranded RNA. Optionally, single-stranded DNA and/or single-stranded RNA are converted to double-stranded forms so that they are included in subsequent processing and analysis steps.

B. Tagging

In some embodiments, the nucleic acid molecules may be tagged with sample indexes and/or molecular barcodes (referred to generally as "tags"). Tags may be incorporated into or otherwise joined to adapters by chemical synthesis, ligation (e.g., blunt-end ligation or sticky-end ligation), or overlap extension polymerase chain reaction (PCR), among other methods. Such adapters may be ultimately joined to the target nucleic acid molecule. In other embodiments, one or more rounds of amplification cycles (e.g., PCR amplification) are generally applied to introduce molecular barcodes and/or sample indexes to a nucleic acid molecule using conventional nucleic acid amplification methods. The amplifications may be conducted in one or more reaction mixtures (e.g., a plurality of microwells in an array). Molecular barcodes and/or sample indexes may be introduced simultaneously, or in any sequential order. In some embodiments, molecular barcodes and/or sample indexes are introduced prior to and/or after sequence capturing steps are performed. In some embodiments, only the molecular barcodes are introduced prior to probe capturing and the sample indexes are introduced after sequence capturing steps are performed. In some embodiments, both the molecular barcodes and the sample indexes are introduced prior to performing probe-based capturing steps. In some embodiments, the sample indexes are introduced after sequence capturing steps are performed. Typically, sequence capturing protocols involve introducing a single-stranded nucleic acid molecule complementary to a targeted nucleic acid sequence, e.g., a coding sequence of a genomic region and mutation of such region is associated with a cancer type.

In some embodiments, the tags may be located at one end or at both ends of the sample nucleic acid molecule. In some embodiments, tags are predetermined or random or semi-random sequence oligonucleotides. In some embodiments, the tags may be less than about 500, 200, 100, 50, 20, 10, 9, 8, 7, 6, 5, 4, 3, 2, or 1 nucleotides in length. The tags may be linked to sample nucleic acids randomly or non-randomly.

In some embodiments, each nucleic acid molecule of a sample or sub-sample is uniquely tagged with a molecular barcode or a combination of molecular barcodes. In other embodiments, a plurality of barcodes may be used such that barcodes are not necessarily unique to one another in the plurality (e.g., non-unique molecular barcodes). In these embodiments, barcodes are generally attached (e.g., by ligation or PCR amplification) to individual molecules such that the combination of the barcode and the sequence it may be attached to creates a unique sequence that may be individually tracked. Detection of non-uniquely tagged barcodes in combination with endogenous sequence information (e.g., the beginning (start) and/or end (stop) portions corresponding to the sequence of the original nucleic acid molecule in the sample, sub-sequences of sequence reads at one or both ends, length of sequence reads, and/or length of the original nucleic acid molecule in the sample) typically allows for the assignment of a unique identity to a particular molecule. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

In some embodiments, molecular barcodes are introduced at an expected ratio of identifiers (e.g., a combination of unique or non-unique barcodes) to molecules in a sample. One example format uses from about 2 to about 1,000,000 different molecular barcodes, or from about 5 to about 150 different molecular barcodes, or from about 20 to about 50 different molecular barcodes, ligated to both ends of a target molecule. Alternatively, from about 25 to about 1,000,000 different barcodes may be used. For example, for 20-50× 20-50 tags, a total of 400-2500 identifiers are created. Such numbers of identifiers are typically sufficient for different molecules having the same start and stop points to have a high probability (e.g., at least 94%, 99.5%, 99.99%, or 99.999%) of receiving different combinations of identifiers. In some embodiments, about 80%, about 90%, about 95% or about 99% of molecules have the same combinations of molecular barcodes.

In some embodiments, the assignment of unique or non-unique molecular barcodes in reactions is performed using methods and systems described in, for example, U.S. Patent Application Nos. 20010053519, 20030152490, and 20110160078, and U.S. Pat. Nos. 6,582,908, 7,537,898, 9,598,731, and 9,902,992 each of which is hereby incorporated by reference in its entirety.

C. Amplification

Sample nucleic acids may be flanked by adapters and amplified by PCR and other amplification methods using nucleic acid primers binding to primer binding sites in adapters flanking a DNA molecule to be amplified. In some embodiments, amplification methods involve cycles of extension, denaturation, and annealing resulting from thermocycling, or can be isothermal as, for example, in transcription mediated amplification. Other examples of amplification methods that may be optionally utilized include the ligase chain reaction, strand displacement amplification, nucleic acid sequence-based amplification, and self-sustained sequence-based replication.

Typically, the amplification reactions generate a plurality of non-uniquely or uniquely tagged nucleic acid amplicons with molecular barcodes and sample indexes at size ranging from about 150 nucleotides (nt), to about 700 nt, from 250 nt to about 350 nt, or from about 320 nt to about 550 nt. In some embodiments, the amplicons have a size of about 180 nt. In some embodiments, the amplicons have a size of about 200 nt.

D. Enrichment

In some embodiments, sequences are enriched prior to sequencing the nucleic acids. Enrichment optionally performed for specific target regions or nonspecifically ("target sequences"). In some embodiments, targeted regions of interest may be enriched with nucleic acid capture probes ("baits") selected for one or more bait set panels using a differential tiling and capture scheme. A differential tiling and capture scheme generally uses bait sets of different relative concentrations to differentially tile (e.g., at different "resolutions") across genomic regions associated with the baits, subject to a set of constraints (e.g., sequencer constraints such as sequencing load, utility of each bait, etc.), and capture the targeted nucleic acids at a desired level for downstream sequencing. These targeted genomic regions of interest optionally include natural or synthetic nucleotide sequences of the nucleic acid construct. In some embodiments, biotin-labeled beads with probes to one or more regions of interest can be used to capture target sequences, and optionally followed by amplification of those regions, to enrich for the regions of interest.

Sequence capture typically involves the use of oligonucleotide probes that hybridize to the target nucleic acid sequence. In some embodiments, a probe set strategy involves tiling the probes across a region of interest. Such probes can be, for example, from about 60 to about 120 nucleotides in length. The set can have a depth (e.g., depth of coverage) of about 2×, 3×, 4×, 5×, 6×, 7×, 8×, 9×, 10×, 15×, 20×, 50×, or more than 50×. The effectiveness of sequence capture generally depends, in part, on the length of the sequence in the target molecule that is complementary (or nearly complementary) to the sequence of the probe.

E. Sequencing

Sample nucleic acids, optionally flanked by adapters, with or without prior amplification are generally subjected to sequencing. Sequencing methods or commercially available formats that are optionally utilized include, for example, Sanger sequencing, high-throughput sequencing, pyrosequencing, sequencing-by-synthesis, single-molecule sequencing, nanopore-based sequencing, semiconductor sequencing, sequencing-by-ligation, sequencing-by-hybridization. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

The sequencing reactions can be performed on one or more nucleic acid fragment types or regions known to contain markers of cancer or of other diseases. The sequencing reactions can also be performed on any nucleic acid fragment present in the sample. The sequence reactions may be performed on at least about 5%, 10%, 15%, 20%, 25%, 30%, 40%, 50%, 60%, 70%, 80%, 90%, 95%, 99%, 99.9%, or 100% of the genome. In other cases, sequence reactions may be performed on less than about 5%, 10%, 15%, 20%, 25%, 30%, 40%, 50%, 60%, 70%, 80%, 90%, 95%, 99%, 99.9%, or 100% of the genome.

Simultaneous sequencing reactions may be performed using multiplex sequencing techniques. In some embodiments, cell-free polynucleotides are sequenced with at least about 1000, 2000, 3000, 4000, 5000, 6000, 7000, 8000, 9000, 10000, 50000, or 100,000 sequencing reactions. In other embodiments, cell-free polynucleotides are sequenced with less than about 1000, 2000, 3000, 4000, 5000, 6000, 7000, 8000, 9000, 10000, 50000, or 100,000 sequencing reactions. Sequencing reactions are typically performed sequentially or simultaneously. Subsequent data analysis is generally performed on all or part of the sequencing reactions. In some embodiments, data analysis is performed on at least about 1000, 2000, 3000, 4000, 5000, 6000, 7000, 8000, 9000, 10000, 50000, or 100,000 sequencing reactions. In other embodiments, data analysis may be performed on less than about 1000, 2000, 3000, 4000, 5000, 6000, 7000, 8000, 9000, 10000, 50000, or 100,000 sequencing reactions. An example of a read depth is from about 1000 to about 50000 reads per locus (e.g., base position).

F. Analysis

Sequencing may generate a plurality of sequencing reads or reads. Sequencing reads or reads may include sequences of nucleotide data less than about 150 bases in length, or less than about 90 bases in length. In some embodiments, reads are between about 80 bases and about 90 bases, e.g., about 85 bases in length. In some embodiments, methods of the present disclosure are applied to very short reads, e.g., less than about 50 bases or about 30 bases in length. Sequencing read data can include the sequence data as well as meta information. Sequence read data can be stored in any suitable file format including, for example, VCF files, FASTA files, or FASTQ files.

FASTA may refer to a computer program for searching sequence databases, and the name FASTA may also refer to a standard file format. For example, FASTA is described by, for example, Pearson & Lipman, 1988, Improved tools for biological sequence comparison, PNAS 85:2444-2448, which is hereby incorporated by reference in its entirety. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There should be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer, as described by, for example, Cock et al. ("The Sanger FASTQ file format for sequences with quality scores, and the Solexa/Illumina FASTQ variants," *Nucleic Acids Res* 38(6):1767-1771, 2009), which is hereby incorporated by reference in its entirety.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of IUPAC ambiguity codes optionally with "-". In an embodiment, the sequence data may use the A, T, C, G, and N characters, optionally including "-" or U as-needed (e.g., to represent gaps or uracil).

In some embodiments, the at least one master sequence read file and the output file are stored as plain text files (e.g., using encoding such as ASCII; ISO/IEC 646; EBCDIC; UTF-8; or UTF-16). A computer system provided by the present disclosure may include a text editor program capable of opening the plain text files. A text editor program may refer to a computer program capable of presenting contents of a text file (such as a plain text file) on a computer screen, allowing a human to edit the text (e.g., using a monitor, keyboard, and mouse). Examples of text editors include, without limitation, Microsoft Word, emacs, pico, vi, BBEdit, and TextWrangler. The text editor program may be capable of displaying the plain text files on a computer screen, showing the meta information and the sequence reads in a human-readable format (e.g., not binary encoded but instead using alphanumeric characters as they may be used in print or human writing).

While methods have been discussed with reference to FASTA or FASTQ files, methods and systems of the present disclosure may be used to compress any suitable sequence file format including, for example, files in the Variant Call Format (VCF) format. A typical VCF file may include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described by, for example, Danecek et al. ("The variant call format and VCFtools," *Bioinformatics* 27(15):2156-2158, 2011), which is hereby incorporated by reference in its entirety. The header section may be treated as the meta information to write to the compressed files and the data section may be treated as the lines, each of which will be stored in a master file only if unique.

Some embodiments provide for the assembly of sequencing reads. In assembly by alignment, for example, the sequencing reads are aligned to each other or aligned to a reference sequence. By aligning each read, in turn to a reference genome, all of the reads are positioned in relationship to each other to create the assembly. In addition, aligning or mapping the sequencing read to a reference sequence can also be used to identify variant sequences within the sequencing read. Identifying variant sequences can be used in combination with the methods and systems described herein to further aid in the diagnosis or prognosis of a disease or condition, or for guiding treatment decisions.

In some embodiments, any or all of the steps are automated. Alternatively, methods of the present disclosure may be embodied wholly or partially in one or more dedicated programs, for example, each optionally written in a compiled language such as C++, then compiled and distributed as a binary. Methods of the present disclosure may be implemented wholly or in part as modules within, or by invoking functionality within, existing sequence analysis platforms. In some embodiments, methods of the present disclosure include a number of steps that are all invoked automatically responsive to a single starting queue (e.g., one or a combination of triggering events sourced from human activity, another computer program, or a machine). Thus, the present disclosure provides methods in which any or the steps or any combination of the steps can occur automatically responsive to a queue. "Automatically" generally means without intervening human input, influence, or interaction (e.g., responsive only to original or pre-queue human activity).

The methods of the present disclosure may also encompass various forms of output, which includes an accurate and sensitive interpretation of a subject's nucleic acid sample. The output of retrieval can be provided in the format of a computer file. In some embodiments, the output is a FASTA file, a FASTQ file, or a VCF file. The output may be processed to produce a text file, or an XML file containing sequence data such as a sequence of the nucleic acid aligned to a sequence of the reference genome. In other embodiments, processing yields output containing coordinates or a string describing one or more mutations in the subject nucleic acid relative to the reference genome. Alignment strings may include Simple UnGapped Alignment Report (SUGAR), Verbose Useful Labeled Gapped Alignment Report (VULGAR), and Compact Idiosyncratic Gapped Alignment Report (CIGAR) (as described by, for example, Ning et al., *Genome Research* 11(10):1725-9, 2001, which is hereby incorporated by reference in its entirety). These strings may be implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file—comprising a CIGAR string (the SAM format is described, e.g., by Li et al., "The Sequence Alignment/Map format and SAMtools," *Bioinformatics,* 25(16):2078-9, 2009, which is hereby incorporated by reference in its entirety). In some embodiments, CIGAR displays or includes gapped alignments one-per-line. CIGAR is a compressed pairwise alignment format reported as a CIGAR string. A CIGAR string may be useful for representing long (e.g., genomic) pairwise alignments. A CIGAR string may be used in SAM format to represent alignments of reads to a reference genome sequence.

A CIGAR string may follow an established motif. Each character is preceded by a number, giving the base counts of the event. Characters used can include M, I, D, N, and S (M=match; I=insertion; D=deletion; N=gap; S=substitution). The CIGAR string defines the sequence of matches/mismatches and deletions (or gaps). For example, the CIGAR string 2MD3M2D2M may indicate that the alignment contains 2 matches, 1 deletion (number 1 is omitted in order to save some space), 3 matches, 2 deletions, and 2 matches.

In some embodiments, a nucleic acid population is prepared for sequencing by enzymatically forming blunt-ends on double-stranded nucleic acids with single-stranded overhangs at one or both ends. In these embodiments, the population is typically treated with an enzyme having a 5'-3' DNA polymerase activity and a 3'-5' exonuclease activity in the presence of the nucleotides (e.g., A, C, G, and T or U). Examples of enzymes or catalytic fragments thereof that may be optionally used include Klenow large fragment and T4 polymerase. At 5' overhangs, the enzyme typically extends the recessed 3' end on the opposing strand until it is flush with the 5' end to produce a blunt end. At 3' overhangs, the enzyme generally digests from the 3' end up to and sometimes beyond the 5' end of the opposing strand. If this digestion proceeds beyond the 5' end of the opposing strand, the gap can be filled in by an enzyme having the same polymerase activity that is used for 5' overhangs. The formation of blunt ends on double-stranded nucleic acids facilitates, for example, the attachment of adapters and subsequent amplification.

In some embodiments, nucleic acid populations are subjected to additional processing, such as the conversion of single-stranded nucleic acids to double-stranded nucleic acids and/or conversion of RNA to DNA (e.g., complementary DNA or cDNA). These forms of nucleic acid are also optionally linked to adapters and amplified.

With or without prior amplification, nucleic acids subject to the process of forming blunt-ends described above, and optionally other nucleic acids in a sample, can be sequenced to produce sequenced nucleic acids. A sequenced nucleic acid can refer either to the sequence of a nucleic acid (e.g., sequence information) or a nucleic acid whose sequence has been determined. Sequencing can be performed so as to provide sequence data of individual nucleic acid molecules in a sample either directly or indirectly from a consensus sequence of amplification products of an individual nucleic acid molecule in the sample.

In some embodiments, double-stranded nucleic acids with single-stranded overhangs in a sample after blunt-end formation are linked at both ends to adapters including barcodes, and the sequencing determines nucleic acid sequences as well as in-line barcodes introduced by the adapters. The blunt-end DNA molecules are optionally ligated to a blunt end of an at least partially double-stranded adapter (e.g., a Y-shaped or bell-shaped adapter). Alternatively, blunt ends of sample nucleic acids and adapters can be tailed with complementary nucleotides to facilitate ligation (for e.g., sticky-end ligation).

The nucleic acid sample is typically contacted with a sufficient number of adapters that there is a low probability (e.g., less than about 1 or 0.1%) that any two copies of the same nucleic acid receive the same combination of adapter barcodes from the adapters linked at both ends. The use of adapters in this manner may permit identification of families of nucleic acid sequences with the same start and stop points on a reference nucleic acid and linked to the same combination of barcodes. Such a family may represent sequences of amplification products of a nucleic acid in the sample before amplification. The sequences of family members can be compiled to derive consensus nucleotide(s) or a complete consensus sequence for a nucleic acid molecule in the original sample, as modified by blunt-end formation and adapter attachment. In other words, the nucleotide occupying a specified position of a nucleic acid in the sample can be determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand may be converted to their complements for purposes of compiling sequences to derive consensus nucleotide(s) or sequences. Some families include only a single member sequence. In this case, this sequence can be taken as the sequence of a nucleic acid in the sample before amplification. Alternatively, families with only a single member sequence can be eliminated from subsequent analysis.

Nucleotide variations (e.g., SNVs or indels) in sequenced nucleic acids can be determined by comparing sequenced nucleic acids with a reference sequence. The reference sequence is often a known sequence, e.g., a known whole or partial genome sequence from a subject (e.g., a whole genome sequence of a human subject). The reference sequence can be, for example, hG19 or hG38. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (e.g., same as in the reference sequence). If the number of sequenced nucleic acids in the subset including a nucleotide variant exceeding a selected threshold, then a variant nucleotide can be called at the designated position. The threshold can be a simple number, such as at least 1, 2, 3, 4, 5, 6, 7, 8, 9, or 10 sequenced nucleic acids within the subset including the nucleotide variant or it can be a ratio, such as at least 0.5, 1, 2, 3, 4, 5, 10, 15, or 20, of sequenced nucleic acids within the subset that include the nucleotide variant, among other possibilities. The comparison can be repeated for any designated position of interest in the reference sequence. Sometimes a comparison can be performed for designated positions occupying at least about 20, 100, 200, or 300 contiguous positions on a reference sequence, e.g., about 20-500, or about 50-300 contiguous positions.

Additional details regarding nucleic acid sequencing, including the formats and applications described herein, are also provided in, for example, Levy et al., Annual Review of Genomics and Human Genetics, 17: 95-115 (2016), Liu et al., J. of Biomedicine and Biotechnology, Volume 2012, Article ID 251364:1-11 (2012), Voelkerding et al., Clinical Chem., 55: 641-658 (2009), MacLean et al., Nature Rev. Microbiol., 7: 287-296 (2009), Astier et al., J Am Chem Soc., 128(5):1705-10 (2006), U.S. Pat. Nos. 6,210,891, 6,258,568, 6,833,246, 7,115,400, 6,969,488, 5,912,148, 6,130,073, 7,169,560, 7,282,337, 7,482,120, 7,501,245, 6,818,395, 6,911,345, 7,501,245, 7,329,492, 7,170,050, 7,302,146, 7,313,308, and 7,476,503, each of which is hereby incorporated by reference in its entirety.

III. Computer Systems

Methods of the present disclosure can be implemented using, or with the aid of, computer systems. For example, such methods may comprise (a) determining a plurality of quantitative measures for the nucleic acid variant from a sample of nucleic acid molecules (e.g., a sample of cfDNA), wherein the plurality of quantitative measures comprises a total allele count and a minor allele count for the nucleic acid variant; (b) identifying an associated variable of the nucleic acid variant from the sample; (c) determining a quantitative value for the associated variable of the nucleic acid variant; (d) generating a statistical model for expected germline mutant allele counts at a genomic locus of the nucleic acid variant; (e) generating a probability value (p-value) for the nucleic acid variant based at least in part on the statistical model for expected germline mutant allele counts, the quantitative value for the associated variable of the nucleic acid variant, and at least one of the plurality of quantitative measures for the nucleic acid variant; and (f) classifying the nucleic acid variant as (i) being of somatic origin when the p-value for the nucleic acid variant is below a predetermined threshold value, or as (ii) being of germline origin when the p-value for the nucleic acid variant is at or above the predetermined threshold value, can be performed with a computer processor.

Figure 4:
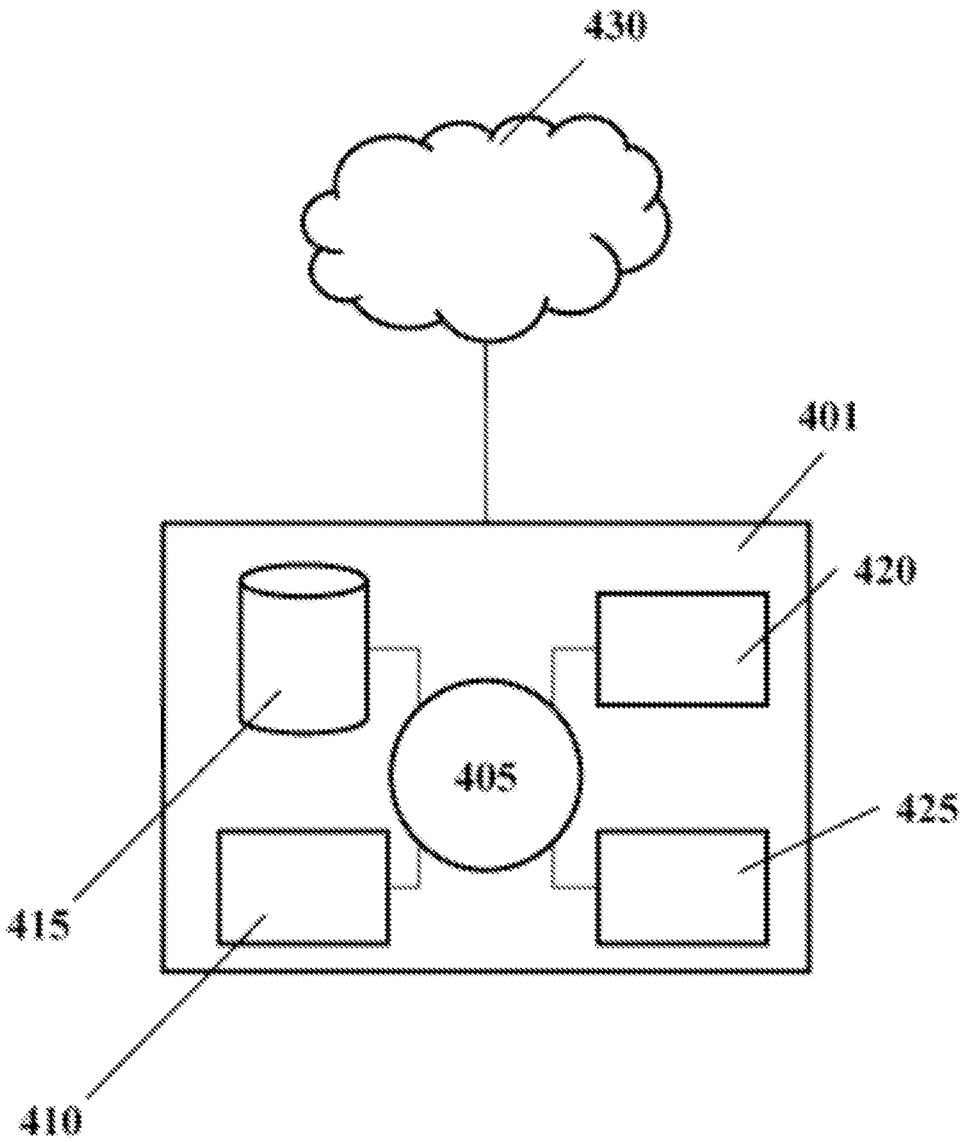
FIG. 4 is a schematic diagram of an example system suitable for use with some embodiments of the disclosure.

FIG. 4 shows a computer system 401 that is programmed or otherwise configured to implement the methods of the present disclosure. The computer system 401 can regulate various aspects sample preparation, sequencing, and/or analysis. In some examples, the computer system 401 is configured to perform sample preparation and sample analysis, including nucleic acid sequencing.

The computer system 401 includes a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage, and/or electronic display adapters. The memory 410, storage unit 415, interface 420, and peripheral devices 425 are in communication with the CPU 405 through a communication network or bus (solid lines), such as a motherboard. The storage unit 415 can be a data storage unit (or data repository) for storing data. The computer system 401 can be operatively coupled to a computer network 430 with the aid of the communication interface 420. The computer network 430 can be the Internet, an internet and/or extranet, or an intranet and/or extranet that is in communication with the Internet. The computer network 430 in some cases is a telecommunication and/or data network. The computer network 430 can include one or more computer servers, which can enable distributed computing, such as cloud computing. The computer network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. Examples of operations performed by the CPU 405 can include fetch, decode, execute, and writeback.

The storage unit 415 can store files, such as drivers, libraries, and saved programs. The storage unit 415 can store programs generated by users and recorded sessions, as well as output(s) associated with the programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet. Data may be transferred from one location to another using, for example, a communication network or physical data transfer (e.g., using a hard drive, thumb drive, or other data storage mechanism).

The computer system 401 can communicate with one or more remote computer systems through the network 430. For instance, the computer system 401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine-readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

In an aspect, the present disclosure provides a non-transitory computer-readable medium comprising computer-executable instructions which, when executed by at least one electronic processor, perform a method comprising: (a) determining a plurality of quantitative measures for the nucleic acid variant from the cfDNA sample, wherein the plurality of quantitative measures comprises a total allele count and a minor allele count for the nucleic acid variant; (b) identifying an associated variable of the nucleic acid variant from the cfDNA sample; (c) determining a quantitative value for the associated variable of the nucleic acid variant; (d) generating a statistical model for expected germline mutant allele counts at a genomic locus of the nucleic acid variant; (e) generating a probability value (p-value) for the nucleic acid variant based at least in part on the statistical model for expected germline mutant allele counts, the quantitative value for the associated variable of the nucleic acid variant, and at least one of the plurality of quantitative measures for the nucleic acid variant; and (f) classifying the nucleic acid variant as (i) being of somatic origin when the p-value for the nucleic acid variant is below a predetermined threshold value, or as (ii) being of germline origin when the p-value for the nucleic acid variant is at or above the predetermined threshold value.

The code can be pre-compiled and configured for use with a machine have a processer adapted to execute the code or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming.

All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as those used across physical interfaces between local devices, through wired and optical landline networks, and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display that comprises a user interface (UI) for providing, for example, one or more results of sample analysis. Examples of UIs include, without limitation, a graphical user interface (GUI) and web-based user interface.

Additional details relating to computer systems and networks, databases, and computer program products are also provided in, for example, Peterson, *Computer Networks: A Systems Approach*, Morgan Kaufmann, 5$^{th}$ Ed. (2011), Kurose, *Computer Networking: A Top Down Approach*, Pearson, 7$^{th}$ Ed. (2016), Elmasri, *Fundamentals of Database Systems*, Addison Wesley, 6$^{th}$ Ed. (2010), Coronel, *Database Systems: Design, Implementation, & Management*, Cengage Learning, 11$^{th}$ Ed. (2014), Tucker, *Programming Languages*, McGraw-Hill Science/Engineering/Math, 2$^{nd}$ Ed. (2006), and Rhoton, *Cloud Computing Architected: Solution Design Handbook*, Recursive Press (2011), each of which is hereby incorporated by reference in its entirety.

IV. Applications

A. Cancer and Other Diseases

In some embodiments, the methods and systems disclosed herein may be used to identify customized or targeted therapies to treat a given disease or condition in patients based on the classification of a nucleic acid variant as being of somatic or germline origin. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic leukemia (CLL), chronic myeloid leukemia (CIVIL), chronic myelomonocytic leukemia (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (scid), sickle cell disease, spinal muscular atrophy, Tay-Sachs, thalassemia, trimethylaminuria, Turner syndrome, velocardiofacial syndrome, WAGR syndrome, Wilson disease, or the like.

B. Therapies and Related Administration

In certain embodiments, the methods disclosed herein relate to identifying and administering customized therapies to patients given the status of a nucleic acid variant as being of somatic or germline origin. In some embodiments, essentially any cancer therapy (e.g., surgical therapy, radiation therapy, chemotherapy, and/or the like) may be included as part of these methods. Typically, customized therapies include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In certain embodiments, the status of a nucleic acid variant from a sample from a subject as being of somatic or germline origin may be compared with a database of comparator results from a reference population to identify customized or targeted therapies for that subject. Typically, the reference population includes patients with the same cancer or disease type as the test subject and/or patients who are receiving, or who have received, the same therapy as the test subject. A customized or targeted therapy (or therapies) may be identified when the nucleic variant and the comparator results satisfy certain classification criteria (e.g., are a substantial or approximate match).

In certain embodiments, the customized therapies described herein are typically administered parenterally (e.g., intravenously or subcutaneously). Pharmaceutical compositions containing a immunotherapeutic agent are typically administered intravenously. Certain therapeutic agents are administered orally. However, customized therapies (e.g., immunotherapeutic agents, etc.) may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

EXAMPLE

Example 1: Determining Whether an EGFR T790M Mutation is of Germline or Somatic Origin Using a Beta Binomial Model Versus a Threshold Approach A set of samples was processed and analyzed using a blood-based DNA assay developed by Guardant Health, Inc. (Redwood City, CA). One of the samples analyzed had a T790M mutation (single-nucleotide variant) in the EGFR gene at genomic position 55249071 on chromosome 7. The mutant allele count (A) and total allele count (B) of the variant were estimated using bioinformatics analysis to be 1,855 and 10,806, respectively. The mutant allele fraction (MAF) of the variant was estimated to be 0.177 (MAF=A/B).

Figure 5A:
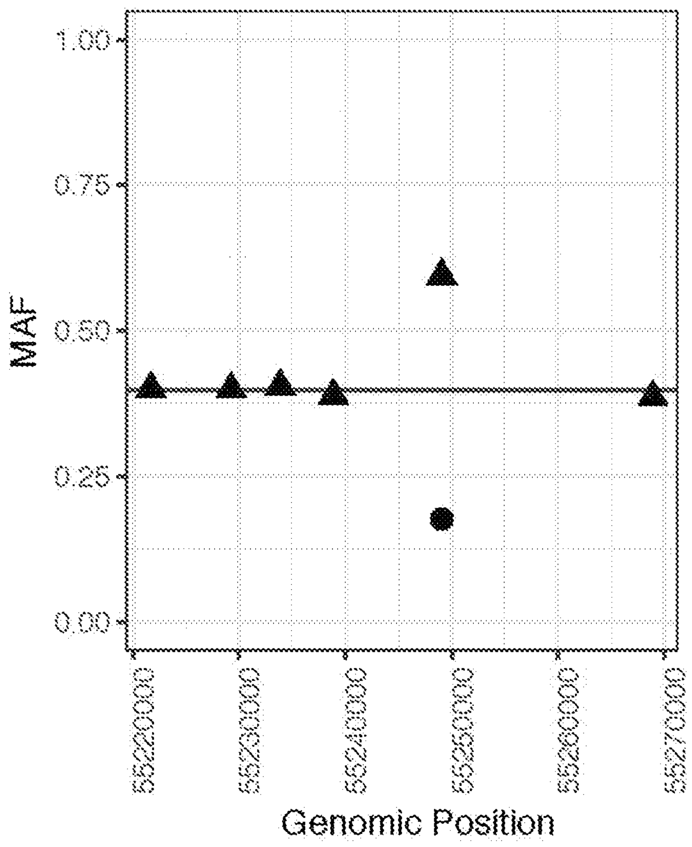
FIG. 5A is a graphical representation of mutant allele fraction (MAF) versus genomic position for the T790M variant and six common germline heterozygous SNPs in EGFR gene.
Figure 5B:
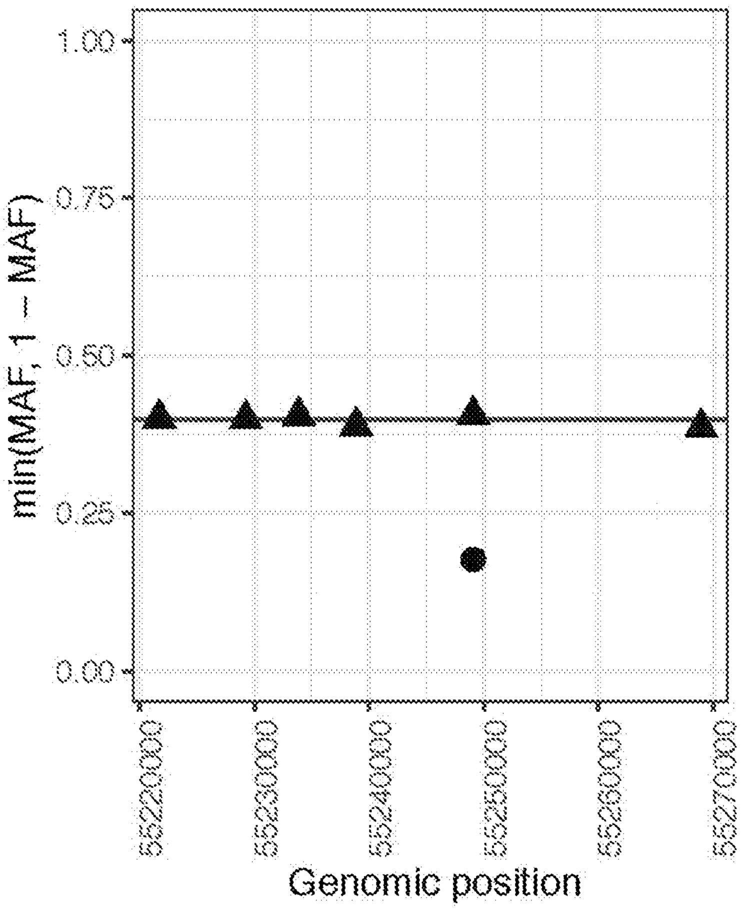
FIG. 5B is a graphical representation of min(MAF, 1−MAF) versus genomic position for the T790M variant and six common germline heterozygous SNPs in EGFR gene.

To determine the origin of the variant, the EGFR gene was used as the bin in the beta binomial model. Six common germline heterozygous SNPs were found in the EGFR gene that were either (i) listed in the ExAC database with a population allele frequency of greater than 0.001 or (ii) listed as known germline heterozygous SNPs in the database of historic sample set with an MAF of less than 0.9. The mutant allele counts, and the total allele counts of these six common germline heterozygous SNPs were used in the beta binomial model and a maximum likelihood estimate (MLE) of a $\mu_{EGFR}$ parameter was estimated using the beta binomial model to be 0.3971. FIG. 5A shows the plot of MAF versus genomic position for the T790M (●) variant and the six common germline heterozygous SNPs (▲). FIG. 5B shows a plot of min(MAF, 1−MAF) versus genomic position for the T790M (●) variant and the six common germline heterozygous SNPs (▲). The $\mu_{EGFR}$ of 0.3971 estimated by the beta binomial model is shown as a solid line in both FIG. 5A and FIG. 5B. The ρ parameter was estimated as the median of the ρ values for germline SNPs in the historic sample set and was calculated to be $9.2\times10^{-5}$. Using these values of $\mu_{EGFR}$ and ρ values, a two-tailed p-value for the T790M variant was calculated to be $2.8\times10^{-302}$. A predetermined threshold of $10^{-16}$ for the p-value was used to identify the origin (e.g., germline or somatic) of the variant. Since the p-value for the T790M variant is less than the predetermined threshold, the T790M variant is determined to be of somatic origin.

As a comparison to using the beta binomial model, the origin of any variant can be determined based on an MAF threshold method, such as by using an MAF of 0.15 as a threshold (e.g., classifying a variant having an MAF less than 0.15 as a somatic variant or a variant having an MAF greater than or equal to 0.15 as a germline variant). The T790M variant, described here, had a measured MAF of 0.177, which is greater than the MAF threshold of 0.15. Thus, the T790M variant would have been erroneously identified to be of germline origin using the MAF threshold method. In contrast, the beta binomial model accurately modeled the local genomic context of the EGFR gene by taking into account any allelic imbalance observed in the EGFR gene and hence correctly identified the variant to be of somatic origin.

Example 2: Next Generation Sequencing Assay for Detection of ctDNA in Early Stage Cancer Patients To address whether genomic analysis of plasma cfDNA could permit simultaneous tumor and germline genotyping, with accurate resolution of tumor-derived variants and germline variants, somatic and germline variants in the EGFR gene, including known germline variants and a group of oncogenic mutations present in 10-20% of NSCLC patients, were studied. One EGFR mutation, T790M, can be detected rarely as a germline variant where its presence has been associated with familial lung cancer. EGFR T790M is more commonly seen as an acquired somatic mutation after a patient with NSCLC develops resistance to EGFR tyrosine kinase inhibitors (TKIs). Lung cancers harboring T790M-mediated resistance after initial therapy exhibit sensitivity to a third-generation EGFR TKI, osimertinib.

A 49-year-old never smoker with a family history of lung cancer presented with metastatic lung adenocarcinoma with primary progression on the second-generation EGFR tyrosine kinase inhibitor (TKI) afatinib. Initial tissue genotyping had shown EGFR L858R and T790M mutations, as well as other somatic alterations in CDKN2A, TP53, and CTNNB1. Due to the L858R mutation in EGFR, first-line afatinib was started. However, the patient returned with progressive brain metastases after only two months of therapy. At the time of referral, plasma next generation sequencing (NGS) demonstrated the previously observed EGFR L858R, TP53, and CTNNB1 variants at an allelic fraction (AF) of 1.4-5.3%, while the EGFR T790M allele was detected at 50.9% AF, as seen in Table 1

TABLE 1

| Alteration | Time 1 (AF) | Time 2 (AF) | Time 3 (AF) |
|---|---|---|---|
| EGFR L858R | 5.3% | 0.6% | 18.1% |
| EGFR T790M | 50.9% | 49.2% | 54.4% |
| EGFR C797S | ND | ND | 1.3% |
| EGFR Q787Q | 51.5% | 48.7% | 54.8% |
| TP53 P278R | 3.8% | ND | 19.7% |

The patient was initiated on osimertinib, an EGFR tyrosine kinase inhibitor (TKI) which is active in the setting of EGFR T790M-mediated resistance to initial EGFR TKIs, and had clinical benefit lasting nine months, at which time scans showed early progression in the lung. Repeat plasma NGS showed the EGFR L858R variant at 0.6% AF but T790M was relatively stable at 49.2% AF. The patient then received investigational therapy on a clinical trial and developed further disease progression. Repeat plasma NGS at this time demonstrated increased levels of the EGFR L858R at 18% AF, T790M at 54% AF, and a third EGFR mutation that mediates acquired resistance to osimertinib, C797S, at 1.3% AF. This mutation may mediate acquired resistance to osimertinib, and the presence of an EGFR T790M mutation at initial diagnosis of the lung cancer, along with its high AF at cfDNA analysis, and the family history of lung cancer, raised the suspicion that the EGFR T790M mutation might have represented a germline risk allele.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, computer readable media, and/or component features, steps, elements, or other aspects thereof can be used in various combinations.

All patents, patent applications, websites, other publications or documents, accession numbers and the like cited herein are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number, if applicable. Likewise, if different versions of a publication, website or the like are published at different times, the version most recently published at the effective filing date of the application is meant, unless otherwise indicated.

What is claimed is:

1. A method for treating a subject having cancer, the method comprising:

tagging a sample obtained from a subject, wherein the sample comprises cell-free deoxyribonucleic acid (cfDNA) molecules;

(a) determining a mutant allele count (A) and a total molecule count (B) of a nucleic acid variant from the tagged cfDNA molecules;

(b) identifying at least one germline heterozygous single nucleotide polymorphism (SNP) within a specified genomic region relative to the nucleic acid variant;

(c) determining a total molecule count (y) and a mutant allele count of the at least one germline heterozygous SNP;

(d) calculating a probability value (p-value) for the nucleic acid variant by:

(i) determining an estimate of $\mu_{bin}$ and ρ from a beta binomial distribution $$(x,y)\sim\text{Beta binomial}(\mu_{bin},\rho),$$

wherein y=a vector of total molecule count of the germline heterozygous SNP(s), with one entry for each germline heterozygous SNP identified in (b);

x=a vector of min (mutant allele count of the germline heterozygous SNP(s), y—mutant allele count of the germline heterozygous SNP(s)), with one entry for each germline heterozygous SNP identified in (b);

$\mu_{bin}$=an estimate of the mutant allele count of germline heterozygous SNPs in a bin, wherein the bin is the specified genomic region relative to the nucleic acid variant; and ρ=an estimate of a dispersion parameter;

(ii) calculating a two-tailed p-value from the below equation $$p\text{-value}=2*\min(Pr_{bb}(x'>A|\mu_{bin},\rho,B),Pr_{bb}(x'<A|\mu_{bin},\rho,B))$$

where $Pr_{bb}$=a probability of beta binomial;

x'=a random variable distributed with the beta binomial distribution;

A=a mutant allele count of the nucleic acid variant;

B=a total molecule count of the nucleic acid variant; and (e) classifying the nucleic acid variant as (i) being of somatic origin when the p-value is below a predetermined threshold value, or as (ii) being of germline origin when the p-value is at or above the predetermined threshold value;

(f) determining that the nucleic acid variant is of somatic origin based on the classification in (e);

(g) comparing the classified nucleic acid variant to one or more comparator results that are indexed with one or more therapies;

(h) identifying one or more customized therapies for treating the cancer in the subject based on the comparison between the classified nucleic acid variant and the comparator results; and (i) administering the one or more customized therapies to the subject, wherein the cfDNA molecules are tagged with molecular barcodes such that different cfDNA molecules can be distinguished based on their endogenous sequence information in combination with at least one molecular barcode, and further wherein the classified nucleic acid variant is EGFR T790M and the one or more customized therapies comprises administering osimertinib as a second line therapy.

2. The method of claim 1, wherein ρ comprises a median value of at least one set of ρ values from a historic sample set.

3. The method of claim 1, wherein ρ is modelled as a function of the GC content of a local genomic context.

4. The method of claim 1, comprising determining a maximum likelihood estimate of $\mu_{bin}$.

5. The method of claim 1, comprising determining a mean estimate of $\mu_{bin}$.

6. The method of claim 1, comprising determining a maximum likelihood estimate of ρ.

7. The method of claim 1, comprising determining a variance estimate of ρ.

8. The method of claim 1, wherein the method comprises generating the predetermined threshold value using a beta-binomial model of expected germline mutant allele counts for the cfDNA molecules.

9. The method of claim 1, wherein the method comprises classifying the somatic or germline origin of multiple nucleic acid variants from a plurality of genomic loci in the sample of cfDNA molecules.

10. The method of claim 1, wherein the method further comprises obtaining sequence information from the cfDNA molecules from the sample from the subject by sequencing.

11. The method of claim 1, wherein the cfDNA molecules are non-uniquely tagged with a limited number of molecular barcodes such that different cfDNA molecules can be distinguished based on their endogenous sequence information in combination with at least one molecular barcode.

12. The method of claim 1, wherein the sample is plasma or serum.

13. The method of claim 12, wherein the sample is obtained from a human subject with cancer.

14. The method of claim 1, wherein the method further comprises generating a report in electronic and/or paper format which provides an indication of the classification of nucleic acid variants as being of either somatic or germline origin.

15. The method of claim 1, wherein the specified genomic region is a region within $10^1$, $10^2$, $10^3$, $10^4$, $10^5$, $10^6$, $10^7$, $10^8$, $10^9$, or $10^{10}$ base pairs of the nucleic acid variant.

16. The method of claim 1, wherein the at least one germline heterozygous SNP comprises a population allele frequency (AF) greater than 0.001.

17. The method of claim 1, wherein the at least one germline heterozygous SNP comprises a mutant allele fraction (MAF) less than 0.9.

18. The method of claim 1, wherein the at least one germline heterozygous SNP comprises at least one non-oncogenic germline heterozygous SNP.

* * * * *